US008742120B2

(12) United States Patent
Pandey et al.

(10) Patent No.: US 8,742,120 B2
(45) Date of Patent: Jun. 3, 2014

(54) METHODS OF PREPARING FACTOR XA INHIBITORS AND SALTS THEREOF

(75) Inventors: Anjali Pandey, Fremont, CA (US); Urvish Pandya, Old Pit (GB)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 338 days.

(21) Appl. No.: 12/970,531

(22) Filed: Dec. 16, 2010

(65) Prior Publication Data

US 2011/0152530 A1 Jun. 23, 2011

Related U.S. Application Data

(60) Provisional application No. 61/287,679, filed on Dec. 17, 2009.

(51) Int. Cl.
*C07D 409/14* (2006.01)

(52) U.S. Cl.
USPC ...................................................... 546/275.1

(58) Field of Classification Search
USPC ...................................................... 546/275.1
See application file for complete search history.

(56) References Cited

U.S. PATENT DOCUMENTS

| | | | |
|---|---|---|---|
| 6,376,515 B2 | 4/2002 | Zhu et al. |
| 6,423,713 B1 | 7/2002 | Anantanarayan et al. |
| 6,835,739 B2 | 12/2004 | Zhu et al. |
| 6,844,367 B1 | 1/2005 | Zhu et al. |
| 6,906,063 B2 | 6/2005 | Scarborough et al. |
| 7,022,695 B2 | 4/2006 | Zhu et al. |
| 7,157,456 B2 | 1/2007 | Straub et al. |
| 7,285,565 B2 | 10/2007 | Zhu et al. |
| 7,312,235 B2 | 12/2007 | Zhu et al. |
| 7,314,874 B2 | 1/2008 | Zhu et al. |
| 7,342,013 B2 | 3/2008 | Zhu et al. |
| 7,521,470 B2 | 4/2009 | Zhu et al. |
| 7,598,276 B2 | 10/2009 | Grant et al. |
| 7,696,352 B2 | 4/2010 | Zhu et al. |
| 7,727,981 B2 | 6/2010 | Zhu et al. |
| 7,727,982 B2 | 6/2010 | Zhu et al. |
| 7,763,608 B2 | 7/2010 | Song et al. |
| 7,767,697 B2 | 8/2010 | Song et al. |
| 8,063,036 B2 | 11/2011 | Zhu et al. |
| 8,063,077 B2 | 11/2011 | Song et al. |
| 2003/0153610 A1 | 8/2003 | Straub et al. |
| 2003/0162690 A1 | 8/2003 | Zhu et al. |
| 2005/0171358 A1 | 8/2005 | Shimozono et al. |
| 2006/0100193 A1 | 5/2006 | Zhu et al. |
| 2007/0043079 A1 | 2/2007 | Habashita et al. |
| 2007/0066615 A1 | 3/2007 | Gerdes et al. |
| 2007/0112039 A1 | 5/2007 | Grant et al. |
| 2007/0185092 A1 | 8/2007 | Zhu et al. |
| 2007/0259924 A1 | 11/2007 | Song et al. |
| 2008/0051578 A1 | 2/2008 | Dahmann et al. |
| 2008/0153876 A1 | 6/2008 | Sinha et al. |
| 2008/0241233 A1 | 10/2008 | Sims et al. |
| 2008/0254036 A1 | 10/2008 | Sinha et al. |
| 2008/0279845 A1 | 11/2008 | Conley et al. |
| 2008/0293704 A1 | 11/2008 | Jia et al. |
| 2009/0098119 A1 | 4/2009 | Lu et al. |
| 2009/0186810 A1 | 7/2009 | Zwaal et al. |
| 2009/0298806 A1 | 12/2009 | Zhu et al. |
| 2010/0063113 A1 | 3/2010 | Grant et al. |
| 2010/0125052 A1 | 5/2010 | Lu et al. |
| 2010/0197929 A1 | 8/2010 | Scarborough et al. |
| 2010/0234352 A1 | 9/2010 | Zhu et al. |
| 2010/0255000 A1 | 10/2010 | Sinha et al. |
| 2011/0015128 A1 | 1/2011 | Sinha et al. |
| 2011/0178135 A1 | 7/2011 | Pandey et al. |
| 2012/0178733 A1 | 7/2012 | Zhu et al. |

FOREIGN PATENT DOCUMENTS

| | | |
|---|---|---|
| CA | 2 453 846 | 1/2003 |
| CA | 2 653 666 | 12/2007 |
| DE | 10322469 | 12/2004 |
| JP | 2000-178243 | 6/2000 |
| WO | WO 99/07379 | 2/1999 |
| WO | WO 99/28317 | 6/1999 |
| WO | WO 01/19788 | 3/2001 |

(Continued)

OTHER PUBLICATIONS

Kirk-Othmer Encyclopedia of Chemical Technology, 8, pp. 95-147 (2002).*
Dorwald, Side Reactions in Organic Synthesis, 2005, Wiley: VCH Weinheim Preface, pp. 1-15 & Chapter 8, pp. 279-308.*
Yu et al., "Physical characterization of, etc.," PSTT, vl. 1(3), 118-127 (1998).*
Vippagunta et al., "Crystalline Solids", Advanced Drug Delivery Reviews 48 (2001) 3-26.*
US 7,479,487, 01/2009, Zhu et al. (withdrawn).
Banker, G.S. et al, "Modern Pharmaceutics, 3rd ed.", Marcel Dekker, New York, 1996, pp. 451 and 596.
In the Pipeline, online, accessed Jun. 16, 2008, "http://pipeline.corante.com/archives/2006/01/24/the_examiner_finally_snaps.php".
Dube and Andrew A. Scholte. Reductive-N-Alkylation of Amides, Carbamates, and Ureas, Tetrahedron Letters, 1999, vol. 40, 2295-2298.
Ostrovsky et al., "Analysis of Activity for Factory Xa Inhibitors Based on Monte Carlo Simulations", *J. Med. Chem.*, 2003, 46, 5691-5699.

(Continued)

*Primary Examiner* — Patricia L Morris
(74) *Attorney, Agent, or Firm* — Sheppard Mullin Richter Hampton LLP

(57) ABSTRACT

The present invention provides for methods of preparing compounds of Formula I or a salt of the compound or a hydrate of the compound or salt thereof that are factor Xa inhibitors.

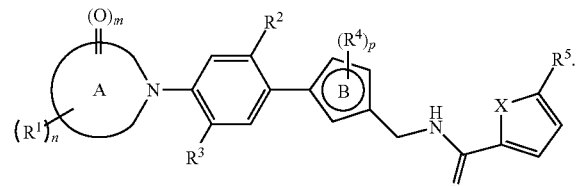

Specifically the present invention provides a method of preparing the compound 5-chloro-N-((1-(4-(2-oxopyridin-1(2H)-yl)phenyl)-1H-imidazol-4-yl)methyl)thiophene-2-carboxamide, or a salt of the compound or a hydrate of the compound or salt thereof.

23 Claims, 5 Drawing Sheets

(56) References Cited

FOREIGN PATENT DOCUMENTS

| | | |
|---|---|---|
| WO | WO 01/21160 | 3/2001 |
| WO | WO 01/47919 | 7/2001 |
| WO | WO 01/64642 | 9/2001 |
| WO | WO 01/64643 | 9/2001 |
| WO | WO 01/91558 | 12/2001 |
| WO | WO 02/00651 | 1/2002 |
| WO | WO 02/079145 | 10/2002 |
| WO | WO 03/000256 | 1/2003 |
| WO | WO 03/008395 | 1/2003 |
| WO | WO 03/059894 | 7/2003 |
| WO | WO 2004/092136 | 10/2004 |
| WO | WO 2004/101531 | 11/2004 |
| WO | WO 2004/101557 | 11/2004 |
| WO | WO 2004/106329 | 12/2004 |
| WO | WO 2005/032468 | 4/2005 |
| WO | WO 2005/034867 | 4/2005 |
| WO | WO 2005/035528 | 4/2005 |
| WO | WO 2005/082892 | 9/2005 |
| WO | WO 2006/002099 | 1/2006 |
| WO | WO 2007/007588 | 1/2007 |
| WO | WO 2007/025940 | 3/2007 |
| WO | WO 2007/056219 | 5/2007 |
| WO | WO 2007/112367 | 10/2007 |
| WO | WO 2007/131179 | 11/2007 |
| WO | WO 2007/137791 | 12/2007 |
| WO | WO 2008/057972 | 5/2008 |
| WO | WO 2008/073670 | 6/2008 |
| WO | WO 2008/086188 | 7/2008 |
| WO | WO 2008/086226 | 7/2008 |
| WO | WO 2008/121721 | 10/2008 |
| WO | WO 2008/127682 | 10/2008 |
| WO | WO 2008/137787 | 11/2008 |
| WO | WO 2009/042962 | 4/2009 |
| WO | WO 2010/056765 | 5/2010 |
| WO | WO/2010/117729 | 10/2010 |
| WO | WO/2011/008885 | 1/2011 |

OTHER PUBLICATIONS

Roehrig et al., "Discovery of the Novel Antithrombotic Agent 5-Chloro-N-(((5S)-2-oxo-3[4-(3-oxomorpholin-4-yl)phenyl]-1,3-oxazol idin-5-yl)methyl)thiophene 2-carboxamide (BAY 59-7939): An Oral, Direct Factor Xa Inhibitor", *J. Med. Chem.*, 2005, 48, 5900-5908.

Qiao et al. "SAR and X-ray structures of enantiopure 1,2-cis-(1R,2S)-cyclopentyldiamine and cyclohexyldiamine derivatives as inhibitors of coagulation Factor Xa" Bioorganic & Medicinal Chemistry Letters, 2007, 17, 4419-4427.

Shi et al. "Cyanoguanidine-based lactam derivatives as a novel class of orally bioavailable factor Xa inhibitors" Bioorganic & Medicinal Chemistry Letters 19, 2009, 4034-4041.

Smallheer et al. "Sulfonamidolactam inhibitors of coagulation factor Xa" Bioorganic & Medicinal Chemistry Letters 2008, 18, 2428-2433.

Song et al. "Substituted Acrylamides as Factor Xa Inhibitors: Improving Bioavailability by PI Modification" Bioorganic & Medicinal Chemistry Letters 12, 2002, 2043-2046.

Wolff, Manfred E. "Burger's Medicinal Chemistry, 5$^{th}$ ed, Part I", John Wiley & Sons, 1995, pp. 975-977.

Daniel Dube and Andrew A. Scholte, Reductive N-Alkylation of Amides, Carbamates, and Ureas, Tetrahedron Letters, vol. 40, 2295-2298, 1999.

* cited by examiner

METHODS OF PREPARING FACTOR XA INHIBITORS AND SALTS THEREOF

CROSS REFERENCE TO RELATED APPLICATIONS

This application claims the benefit under 35 U.S.C. §119(e) of U.S. Provisional Application Ser. No. 61/287,679 filed on Dec. 17, 2009, which is hereby incorporated by reference in its entirety.

BACKGROUND OF THE INVENTION

1. Field of the Invention

This invention is directed to methods for preparing factor Xa inhibitors and salts thereof.

2. State of the Art

Factor Xa is a serine protease, the activated form of its precursor factor X, and a member of the calcium ion binding, gamma carboxyglutamic acid (GLA)-containing, vitamin K dependent, blood coagulation factors. Factor Xa appears to have a single physiologic substrate, namely prothrombin. Since one molecule of factor Xa may be able to generate greater than 1000 molecules of thrombin (Mann, et al., *J. Thrombosis. Haemostasis* 1: 1504-1514, 2003), direct inhibition of factor Xa as a way of indirectly inhibiting the formation of thrombin has been considered an efficient anticoagulant strategy.

Several classes of small molecule factor Xa inhibitors have been reported, for example, those described in U.S. Pat. Nos. 7,521,470, 7,696,352, and 7,763,608, U.S. Patent Application Publication Nos. 2007/0066615, 2008/0293704, and 2008/0051578, all of which are incorporated by reference in their entirety.

SUMMARY OF THE INVENTION

In one aspect, the invention is directed to methods of preparing a compound of Formula I or a salt thereof or a hydrate of the compound or salt thereof:

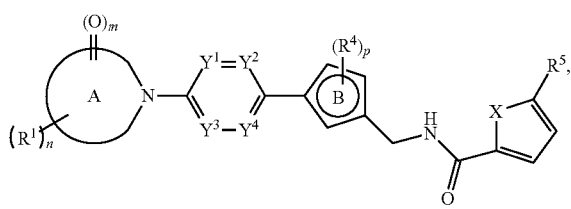

I comprising contacting a compound of formula I-A

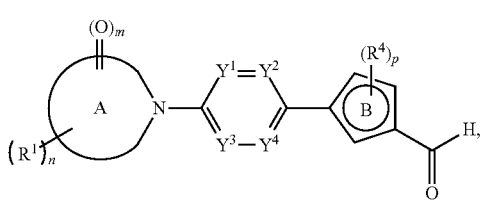

I-A with a compound of formula I-B

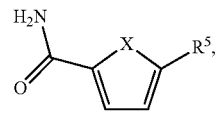

I-B under reaction conditions to form the compound of formula I or the salt or the hydrate; and wherein:

ring A is 5-, 6-, or 7-membered nitrogen-containing heterocycloalkyl or 5-, 6-, or 7-membered nitrogen-containing heteroaryl;

ring B is a 5-membered nitrogen-containing heteroaryl;

$Y^1$, $Y^2$, $Y^3$, and $Y^4$ are independently $CR^2$ or N, provided that at least two of $Y^1$, $Y^2$, $Y^3$, and $Y^4$ are $CR^2$;

each $R^1$ is independently selected from the group consisting of $C_{1-8}$ alkyl, halo, nitro, cyano, $OR^{12}$, $SR^{12}$, $S(O)R^{12}$, $S(O)_2R^{12}$, $C(O)R^{12}$, $OC(O)R^{12}$, $OC(O)NHR^{12}$, $CO_2R^{12}$, $NHS(O)_2R^{12}$, $S(O)_2NHR^{12}$, $NHC(O)NHR^{12}$, $C(O)NHR^{12}$, $NHC(O)R^{12}$, $NHC(O)OR^{12}$, aryl, heteroaryl and heterocycloalkyl, wherein each of the $C_{1-8}$ alkyl, aryl, heteroaryl and heterocycloalkyl are optionally substituted with 1 to 3 $R^{11}$;

each $R^2$ is independently selected from the group consisting of hydrogen, $C_{1-8}$ alkyl, halo, nitro, cyano, $OR^{12}$, $SR^{12}$, $S(O)R^{12}$, $S(O)_2R^{12}$, $NHS(O)_2R^{12}$, $S(O)_2NHR^{12}$, $S(O)_2NR^{12}R^{12}$, $NHC(O)NHR^{12}$, $NHC(O)NR^{12}R^{12}$, $C(O)NHR^{12}$, $C(O)NR^{12}R^{12}$, $C(O)R^{12}$, $OC(O)R^{12}$, $OC(O)NHR^{12}$, $OC(O)NR^{12}R^{12}$, $CO_2R^{12}$, $NHC(O)R^{12}$, $NHC(O)OR^{12}$, aryl, heteroaryl and heterocycloalkyl, wherein each of the $C_{1-8}$ alkyl, aryl, heteroaryl and heterocycloalkyl are optionally substituted with 1 to 3 $R^{11}$;

$R^4$ is independently selected from the group consisting of alkyl, halo, hydroxy, $C_{1-4}$ alkoxy, $SR^{12}$, $S(O)R^{12}$, $S(O)_2R^{12}$, $C(O)R^{12}$, $OC(O)R^{12}$, $OC(O)NHR^{12}$, $CO_2R^{12}$, $NHS(O)_2R^{12}$, $S(O)_2NHR^{12}$, $NHC(O)NHR^{12}$, $C(O)NHR^{12}$, $NHC(O)R^{12}$, $NHC(O)OR^{12}$, aryl, heteroaryl, and heterocycloalkyl, wherein the alkyl, aryl, heteroaryl, and heterocycloalkyl are optionally substituted with 1 to 3 $R^{11}$;

X is S or O;

$R^5$ is selected from the group consisting of halo, $C_{1-4}$ alkyl, $C_{2-4}$ alkenyl and $C_{2-4}$ alkynyl;

m is 0, 1, or 2;

n is 0, 1, 2, 3, or 4;

p is 0, 1, 2, or 3;

each $R^{11}$ is independently selected from the group consisting of halo, oxo, nitro, cyano, carboxyl, $C_{1-4}$ alkyl, $C_{1-4}$ haloalkyl, $OR^{12}$, $SR^{12}$, $S(O)R^{12}$, $S(O)_2R^{12}$, $NHS(O)_2R^{12}$, $S(O)_2NHR^{12}$, $S(O)_2NR^{12}R^{12}$, $C(O)R^{12}$, $OC(O)R^{12}$, $OC(O)NHR^{12}$, $OC(O)NR^{12}R^{12}$, $CO_2R^{12}$, $NHC(O)R^{12}$, $NHC(O)NHR^{12}$, $NHC(O)NR^{12}R^{12}$, $C(O)NHR^{12}$, $C(O)NR^{12}R^{12}$, $NHC(O)OR^{12}$, $C_{3-6}$ cycloalkyl, aryl, heterocycloalkyl, and heteroaryl, wherein the $C_{1-4}$ alkyl, heterocycloalkyl and heteroaryl are optionally substituted with 1 to 3 substituents independently selected from the group consisting of halo, nitro, cyano, $OR^{12}$, $SR^{12}$, $S(O)R^{12}$, $S(O)_2R^{12}$, $NHS(O)_2R^{12}$, $S(O)_2NHR^{12}$, $S(O)_2NR^{12}R^{12}$, $NHC(O)NHR^{12}$, $C(O)NHR^{12}$, $C(O)NR^{12}R^{12}$, $C(O)R^{12}$, $OC(O)R^{12}$, $OC(O)NHR^{12}$, $OC(O)NR^{12}R^{12}$, $CO_2R^{12}$, $NHC(O)R^{12}$, $NHC(O)OR^{12}$, $C_{1-4}$ alkyl, $C_{1-4}$ haloalkyl, hydroxy, $C_{1-4}$ alkoxy, $C_{3-6}$ cycloalkyl, heterocycloalkyl, aryl, and heteroaryl;

each $R^{12}$ is independently selected from the group consisting of alkyl, cycloalkyl, aryl, heteroaryl, and heterocycloalkyl, wherein the alkyl, cycloalkyl, aryl, heteroaryl, and heterocycloalkyl are optionally substituted with 1 to 3 substituents independently selected from the group consisting of halo, oxo, nitro, cyano, carboxyl, carboxyl ester, $C_{1-4}$ alkyl, $C_{1-4}$ haloalkyl, $OR^{13}$, $SR^{13}$, $S(O)R^{13}$, $S(O)_2R^{13}$, $NHS(O)_2R^{13}$, $S(O)_2NHR^{13}$, $S(O)_2NR^{13}R^{13}$, $C(O)R^{13}$, $CO_2R^{13}$, $NHC(O)R^{13}$, $NHC(O)NHR^{13}$, $NHC(O)NR^{13}R^{13}$, $C(O)NHR^{13}$, $OC(O)NHR^{13}$, $OC(O)NR^{13}R^{13}$, $C(O)NR^{13}R^{13}$, $NHC(O)OR^{13}$, heterocycloalkyl, and heteroaryl; or two $R^{12}$ attached to the same nitrogen together with nitrogen attached thereto form a heterocycloalkyl optionally substituted with oxo or $C_{1-4}$ alkyl; and each $R^{13}$ is independently $C_{1-4}$ alkyl optionally substituted with from 1 to 2 substituents independently selected from the group consisting of halo, nitro, cyano, hydroxyl, alkoxy, carboxyl and carboxyl ester; or two $R^{13}$ attached to the same nitrogen together with nitrogen attached thereto form a heterocycloalkyl optionally substituted with oxo or $C_{1-4}$ alkyl.

In one aspect, the invention is directed to methods of preparing a compound of Formula Ia or a salt thereof or a hydrate of the compound or the salt thereof:

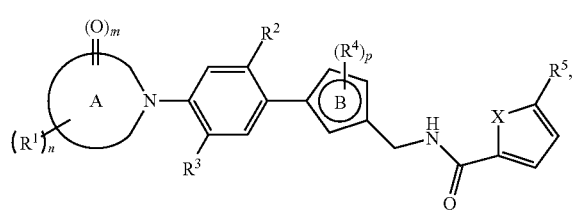

Ia comprising contacting a compound of Formula I-Aa

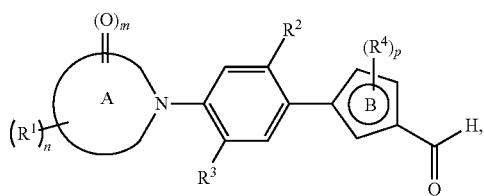

I-Aa with a compound of Formula I-B

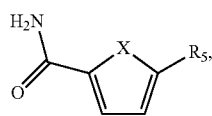

I-B under reaction conditions to form the compound of Formula Ia or the salt or the hydrate; and wherein:

ring A is 5-, 6-, or 7-membered nitrogen-containing heterocycloalkyl or 5-, 6-, or 7-membered nitrogen-containing heteroaryl;

ring B is a 5-membered nitrogen-containing heteroaryl;

each $R^1$ is independently selected from the group consisting of $C_{1-8}$ alkyl, halo, nitro, cyano, $OR^{12}$, $SR^{12}$, $S(O)R^{12}$, $S(O)_2R^{12}$, $C(O)R^{12}$, $OC(O)R^{12}$, $OC(O)NHR^{12}$, $OC(O)NR^{12}R^{12}$, $CO_2R^{12}$, $NHS(O)_2R^{12}$, $S(O)_2NHR^{12}$, $S(O)_2NR^{12}R^{12}$, $NHC(O)NHR^{12}$, $NHC(O)NR^{12}R^{12}$, $C(O)NHR^{12}$, $C(O)NR^{12}R^{12}$, $NHC(O)R^{12}$, $NHC(O)OR^{12}$, aryl, heteroaryl and heterocycloalkyl, wherein each of the $C_{1-8}$ alkyl, aryl, heteroaryl and heterocycloalkyl are optionally substituted with 1 to 3 $R^{11}$;

$R^2$ and $R^3$ are independently selected from the group consisting of hydrogen, $C_{1-8}$ alkyl, halo, nitro, cyano, $OR^{12}$, $SR^{12}$, $S(O)R^{12}$, $S(O)_2R^{12}$, $NHS(O)_2R^{12}$, $S(O)_2NHR^{12}$, $S(O)_2NR^{12}R^{12}$, $NHC(O)NHR^{12}$, $NHC(O)NR^{12}R^{12}$, $C(O)NHR^{12}$, $C(O)NR^{12}R^{12}$, $C(O)R^{12}$, $OC(O)R^{12}$, $OC(O)NHR^{12}$, $OC(O)NR^{12}R^{12}$, $CO_2R^{12}$, $NHC(O)R^{12}$, $NHC(O)OR^{12}$, aryl, heteroaryl and heterocycloalkyl, wherein each of the $C_{1-8}$ alkyl, aryl, heteroaryl and heterocycloalkyl are optionally substituted with 1 to 3 $R^{11}$;

each $R^4$ is independently selected from the group consisting of alkyl, halo, hydroxy, $C_{1-4}$ alkoxy, $SR^{12}$, $S(O)R^{12}$, $S(O)_2R^{12}$, $C(O)R^{12}$, $OC(O)R^{12}$, $OC(O)NHR^{12}$, $CO_2R^{12}$, $NHS(O)_2R^{12}$, $S(O)_2NHR^{12}$, $NHC(O)NHR^{12}$, $C(O)NHR^{12}$, $NHC(O)R^{12}$, $NHC(O)OR^{12}$, aryl, heteroaryl, and heterocycloalkyl, wherein the alkyl, aryl, heteroaryl, and heterocycloalkyl are optionally substituted with 1 to 3 $R^{11}$;

X is S or O;

$R^5$ is selected from the group consisting of halo, $C_{1-4}$ alkyl, $C_{2-4}$ alkenyl and $C_{2-4}$ alkynyl;

m is 0, 1, or 2;

n is 0, 1, 2, 3, or 4;

p is 0, 1, 2, or 3;

each $R^{11}$ is independently selected from the group consisting of halo, oxo, nitro, cyano, carboxyl, $C_{1-4}$ alkyl, $C_{1-4}$ haloalkyl, $OR^{12}$, $SR^{12}$, $S(O)R^{12}$, $S(O)_2R^{12}$, $NHS(O)_2R^{12}$, $S(O)_2NHR^{12}$, $S(O)_2NR^{12}R^{12}$, $C(O)R^{12}$, $OC(O)R^{12}$, $OC(O)NHR^{12}$, $OC(O)NR^{12}R^{12}$, $CO_2R^{12}$, $NHC(O)R^{12}$, $NHC(O)NHR^{12}$, $NHC(O)NR^{12}R^{12}$, $C(O)NHR^{12}$, $C(O)NR^{12}R^{12}$, $NHC(O)OR^{12}$, $C_{3-6}$ cycloalkyl, aryl, heterocycloalkyl, and heteroaryl, wherein the $C_{1-4}$ alkyl, heterocycloalkyl and heteroaryl are optionally substituted with 1 to 3 substituents independently selected from the group consisting of halo, nitro, cyano, $OR^{12}$, $SR^{12}$, $S(O)R^{12}$, $S(O)_2R^{12}$, $NHS(O)_2R^{12}$, $S(O)_2NHR^{12}$, $S(O)_2NR^{12}R^{12}$, $NHC(O)NHR^{12}$, $C(O)NHR^{12}$, $C(O)NR^{12}R^{12}$, $C(O)R^{12}$, $OC(O)R^{12}$, $OC(O)NHR^{12}$, $OC(O)NR^{12}R^{12}$, $CO_2R^{12}$, $NHC(O)R^{12}$, $NHC(O)OR^{12}$, $C_{1-4}$ alkyl, $C_{1-4}$ haloalkyl, hydroxy, $C_{1-4}$ alkoxy, $C_{3-6}$ cycloalkyl, heterocycloalkyl, aryl, and heteroaryl;

each $R^{12}$ is independently selected from the group consisting of alkyl, cycloalkyl, aryl, heteroaryl, and heterocycloalkyl, wherein the alkyl, cycloalkyl, aryl, heteroaryl, and heterocycloalkyl are optionally substituted with 1 to 3 substituents independently selected from the group consisting of halo, oxo, nitro, cyano, carboxyl, carboxyl ester, $C_{1-4}$ alkyl, $C_{1-4}$ haloalkyl, $OR^{13}$, $SR^{13}$, $S(O)R^{13}$, $S(O)_2R^{13}$, $NHS(O)_2R^{13}$, $S(O)_2NHR^{13}$, $S(O)_2NR^{13}R^{13}$, $C(O)R^{13}$, $CO_2R^{13}$, $NHC(O)R^{13}$, $NHC(O)NHR^{13}$, $NHC(O)NR^{13}R^{13}$, $C(O)NHR^{13}$, $OC(O)NHR^{13}$, $OC(O)NR^{13}R^{13}$, $C(O)NR^{13}R^{13}$, $NHC(O)OR^{13}$, heterocycloalkyl, and heteroaryl; or two $R^{12}$ attached to the same nitrogen together with nitrogen attached thereto form a heterocycloalkyl optionally substituted with oxo or $C_{1-4}$ alkyl; and each $R^{13}$ is independently $C_{1-4}$ alkyl optionally substituted with from 1 to 2 substituents independently selected from the group consisting of halo, nitro, cyano, hydroxyl, alkoxy, carboxyl and carboxyl ester; or two $R^{13}$ attached to the same nitrogen together with nitrogen attached thereto form a heterocycloalkyl optionally substituted with oxo or $C_{1-4}$ alkyl.

In another aspect, this invention provides a method of preparing a compound of Formula II or a salt thereof or a hydrate of the compound or the salt thereof:

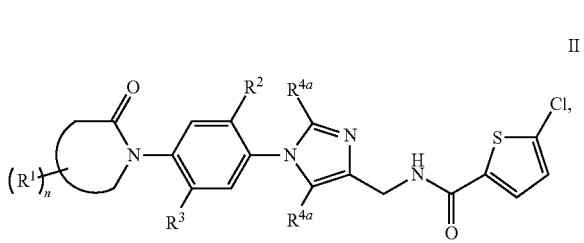

comprising contacting a compound of Formula II-A

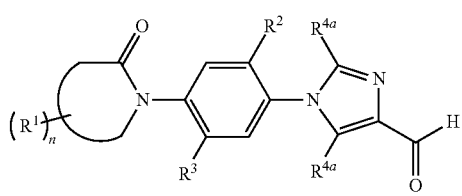

with a compound of Formula II-B

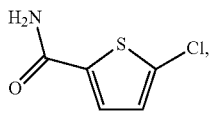

under reaction conditions to form the compound of Formula II or the salt or the hydrate; and wherein:

the group

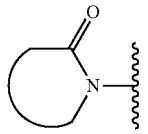

is selected from the group consisting of:

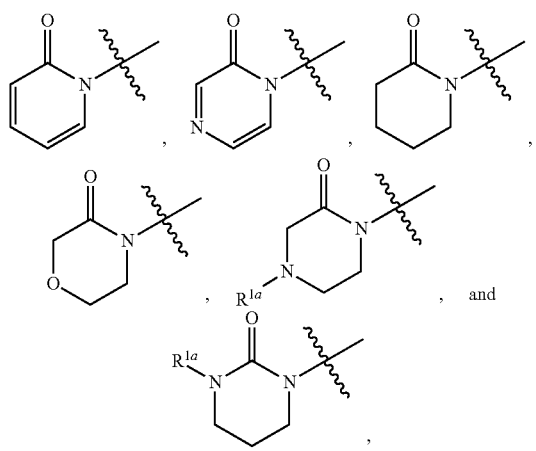

, $R^{1a}$ is hydrogen or $R^1$;

each $R^1$ is independently selected from the group consisting of $C_{1-8}$ alkyl, halo, nitro, cyano, $OR^{12}$, $SR^{12}$, $S(O)R^{12}$, $S(O)_2R^{12}$, $C(O)R^{12}$, $OC(O)R^{12}$, $OC(O)NHR^{12}$, $OC(O)NR^{12}R^{12}$, $CO_2R^{12}$, $NHS(O)_2R^{12}$, $S(O)_2NHR^{12}$, $S(O)_2NR^{12}R^{12}$, $NHC(O)NHR^{12}$, $NHC(O)NR^{12}R^{12}$, $C(O)NHR^{12}$, $C(O)NR^{12}R^{12}$, $NHC(O)R^{12}$, $NHC(O)OR^{12}$, aryl, heteroaryl and heterocycloalkyl, wherein each of the $C_{1-8}$ alkyl, aryl, heteroaryl and heterocycloalkyl are optionally substituted with 1 to 3 $R^{11}$;

$R^2$ and $R^3$ are independently selected from the group consisting of hydrogen, $C_{1-8}$ alkyl, halo, nitro, cyano, $OR^{12}$, $SR^{12}$, $S(O)R^{12}$, $S(O)_2R^{12}$, $NHS(O)_2R^{12}$, $S(O)_2NHR^{12}$, $S(O)_2NR^{12}R^{12}$, $NHC(O)NHR^{12}$, $NHC(O)NR^{12}R^{12}$, $C(O)NHR^{12}$, $C(O)NR^{12}R^{12}$, $C(O)R^{12}$, $OC(O)R^{12}$, $OC(O)NHR^{12}$, $OC(O)NR^{12}R^{12}$, $CO_2R^{12}$, $NHC(O)R^{12}$, $NHC(O)OR^{12}$, aryl, heteroaryl and heterocycloalkyl, wherein each of the $C_{1-8}$ alkyl, aryl, heteroaryl and heterocycloalkyl are optionally substituted with 1 to 3 $R^{11}$;

each $R^{4a}$ is independently hydrogen or $R^4$; $R^4$ is independently selected from the group consisting of alkyl, halo, hydroxy, $C_{1-4}$ alkoxy, $SR^{12}$, $S(O)R^{12}$, $S(O)_2R^{12}$, $C(O)R^{12}$, $OC(O)R^{12}$, $OC(O)NHR^{12}$, $CO_2R^{12}$, $NHS(O)_2R^{12}$, $S(O)_2NHR^{12}$, $NHC(O)NHR^{12}$, $C(O)NHR^{12}$, $NHC(O)R^{12}$, $NHC(O)OR^{12}$, aryl, heteroaryl, and heterocycloalkyl, wherein the alkyl, aryl, heteroaryl, and heterocycloalkyl are optionally substituted with 1 to 3 $R^{11}$;

each $R^{11}$ is independently selected from the group consisting of halo, oxo, nitro, cyano, carboxyl, carboxyl ester, $C_{1-4}$ alkyl, $C_{1-4}$ haloalkyl, $OR^{12}$, $SR^{12}$, $S(O)R^{12}$, $S(O)_2R^{12}$, $NHS(O)_2R^{12}$, $S(O)_2NHR^{12}$, $S(O)_2NR^{12}R^{12}$, $C(O)R^{12}$, $OC(O)R^{12}$, $OC(O)NHR^{12}$, $OC(O)NR^{12}R^{12}$, $CO_2R^{12}$, $NHC(O)R^{12}$, $NHC(O)NHR^{12}$, $NHC(O)NR^{12}R^{12}$, $C(O)NHR^{12}$, $C(O)NR^{12}R^{12}$, $NHC(O)OR^{12}$, $C_{3-6}$ cycloalkyl, aryl, heterocycloalkyl, and heteroaryl, wherein the $C_{1-4}$ alkyl, heterocycloalkyl and heteroaryl are optionally substituted with 1 to 3 substituents independently selected from the group consisting of halo, nitro, cyano, $OR^{12}$, $SR^{12}$, $S(O)R^{12}$, $S(O)_2R^{12}$, $NHS(O)_2R^{12}$, $S(O)_2NHR^{12}$, $S(O)_2NR^{12}R^{12}$, $NHC(O)NHR^{12}$, $C(O)NHR^{12}$, $C(O)NR^{12}R^{12}$, $C(O)R^{12}$, $OC(O)R^{12}$, $OC(O)NHR^{12}$, $OC(O)NR^{12}R^{12}$, $CO_2R^{12}$, $NHC(O)R^{12}$, $NHC(O)OR^{12}$, $C_{1-4}$ alkyl, $C_{1-4}$ haloalkyl, hydroxy, $C_{1-4}$ alkoxy, $C_{3-6}$ cycloalkyl, heterocycloalkyl, aryl, and heteroaryl;

$R^{12}$ is selected from the group consisting of alkyl, cycloalkyl, aryl, and heterocycloalkyl, wherein the alkyl, cycloalkyl, aryl, heteroaryl, and heterocycloalkyl are optionally substituted with 1 to 3 substituents independently selected from the group consisting of halo, oxo, nitro, cyano, carboxyl, carboxyl ester, $C_{1-4}$ alkyl, $C_{1-4}$ haloalkyl, $OR^{13}$, $SR^{13}$, $S(O)R^{13}$, $S(O)_2R^{13}$, $NHS(O)_2R^{13}$, $S(O)_2NHR^{13}$, $S(O)_2NR^{13}R^{13}$, $C(O)R^{13}$, $CO_2R^{13}$, $NHC(O)R^{13}$, $NHC(O)NHR^{13}$, $NHC(O)NR^{13}R^{13}$, $C(O)NHR^{13}$, $OC(O)NHR^{13}$, $OC(O)NR^{13}R^{13}$, $C(O)NR^{13}R^{13}$, $NHC(O)OR^{13}$, heterocycloalkyl, and heteroaryl; or two $R^{12}$ attached to the same nitrogen together with nitrogen attached thereto form a heterocycloalkyl optionally substituted with oxo or $C_{1-4}$ alkyl;

each $R^{13}$ is independently $C_{1-4}$ alkyl optionally substituted with from 1 to 2 substituents independently selected from the group consisting of halo, nitro, cyano, hydroxyl, alkoxy, carboxyl and carboxyl ester; or two $R^{13}$ attached to the same nitrogen together with nitrogen attached thereto form a heterocycloalkyl optionally substituted with oxo or $C_{1-4}$ alkyl; and n is 0, 1, 2, 3, or 4, provided that when $R^{1a}$ is not hydrogen, then n is 0, 1, 2, or 3.

In another aspect, this invention provides a method of preparing a compound of Formula III or a salt thereof or a hydrate of the compound or the salt thereof

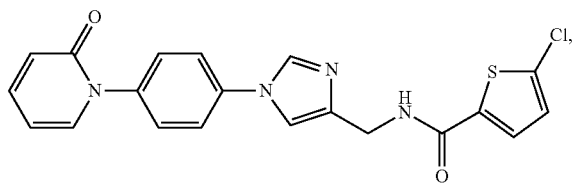

comprising contacting a compound of Formula III-A

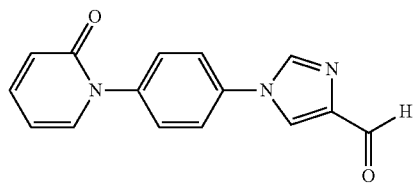

with a compound of Formula III-B

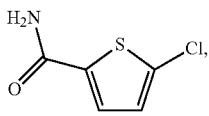

under reaction conditions to form the compound of Formula III or the salt or the hydrate.

In another aspect, this invention provides a method of preparing a salt of a compound of Formula III or a hydrate of the salt

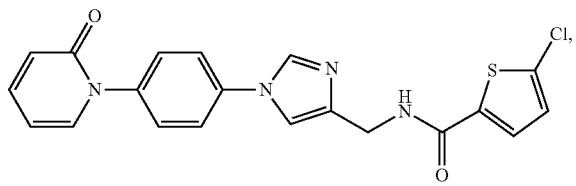

comprising contacting a compound of formula III-A

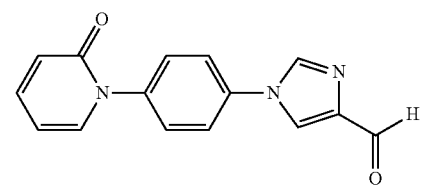

with a compound of formula III-B

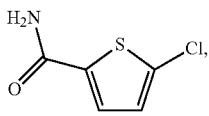

under reaction conditions to form the compound of formula III;

isolating the compound of Formula III under isolating conditions wherein the compound of Formula III is isolated as a free base; and forming the salt of the compound of Formula III under salt forming conditions comprising contacting the compound of Formula III with at least a molar equivalent of an acid in a solvent.

In another aspect, this invention provides intermediates for preparing a compounds of Formula I, Ia, II, or III, and process for preparing the intermediates.

This and other embodiments will be further described in the text that follows.

DETAILED DESCRIPTION OF THE INVENTION

Figure 1:
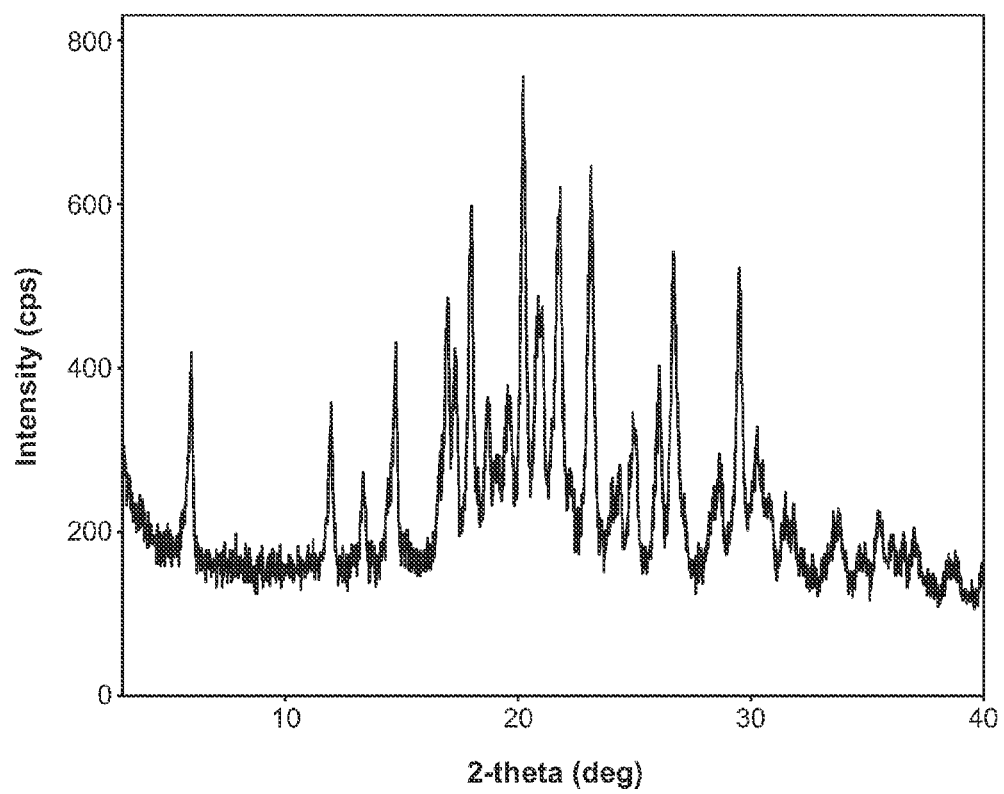
FIG. 1 provides an X-ray powder diffraction (XRPD) pattern of crystalline Form A of the mesylate salt of the compound of Formula III.

As used herein, the following definitions shall apply unless otherwise indicated.

Definitions

As used in the specification and claims, the singular form "a", "an" and "the" include plural references unless the context clearly dictates otherwise.

As used herein, the term "comprising" is intended to mean that the compositions and methods include the recited elements, but not excluding others. "Consisting essentially of" when used to define compositions and methods, shall mean excluding other elements of any essential significance to the combination. For example, a composition consisting essentially of the elements as defined herein would not exclude other elements that do not materially affect the basic and novel characteristic(s) of the claimed invention. "Consisting of" shall mean excluding more than trace amount of other ingredients and substantial method steps recited. Embodiments defined by each of these transition terms are within the scope of this invention.

"Alkyl" refers to monovalent saturated aliphatic hydrocarbyl groups having from 1 to 10 carbon atoms and preferably 1 to 6 carbon atoms. When $C_y$ alkyl or $C_{y-z}$ alkyl is used, y and z indicate the number of carbon atoms in the alkyl group. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3)_2CH$—), n-butyl ($CH_3CH_2CH_2CH_2$—), isobutyl (($CH_3)_2CHCH_2$—), sec-butyl (($CH_3)(CH_3CH_2)CH$—), t-butyl (($CH_3)_3C$—), n-pentyl ($CH_3CH_2CH_2CH_2CH_2$—), and neopentyl (($CH_3)_3CCH_2$—).

"Alkenyl" refers to straight or branched hydrocarbyl groups having from 2 to 6 carbon atoms and preferably 2 to 4 carbon atoms and having at least 1 and preferably from 1 to 2 sites of vinyl (>C=C<) unsaturation. Such groups are exemplified, for example, by vinyl, allyl, and but-3-en-1-yl. Included within this term are the cis and trans isomers or mixtures of these isomers.

"Alkynyl" refers to straight or branched monovalent hydrocarbyl groups having from 2 to 6 carbon atoms and preferably 2 to 3 carbon atoms and having at least 1 and preferably from 1 to 2 sites of acetylenic (—C≡C—) unsaturation. Examples of such alkynyl groups include acetylenyl (—C≡CH), and propargyl (—$CH_2$C≡CH).

"Alkoxy" refers to the group —O-alkyl wherein alkyl is defined herein. Alkoxy includes, by way of example, methoxy, ethoxy, n-propoxy, isopropoxy, n-butoxy, t-butoxy, sec-butoxy, and n-pentoxy.

"Amino" refers to the group —$NH_2$.

"Aryl" refers to a monovalent aromatic carbocyclic group of from 6 to 14, preferably from 6 to 10, carbon atoms having a single ring (e.g., phenyl) or multiple condensed rings (e.g., naphthyl or anthryl) which condensed rings may or may not be aromatic (e.g., 2-benzoxazolinone, 2H-1,4-benzoxazin-3 (4H)-one-7-yl, and the like) provided that the point of attachment is at an aromatic carbon atom. Preferred aryl groups include phenyl and naphthyl.

"Carbonyl" refers to the divalent group —C(O)— which is equivalent to —C(=O)—.

"Carboxy" or "carboxyl" refers to —COOH or salts thereof.

"Carboxy ester" or "carboxyl ester" refers to —$COOR^e$, wherein $R^e$ is alkyl or alkyl substituted with 1-3 substituents selected from the group consisting of aryl, heteroaryl, cycloalkyl, and heterocycloalkyl.

"Cyano" refers to the group —CN.

"Cycloalkyl" refers to cyclic alkyl groups of from 3 to 10 carbon atoms having single or multiple cyclic rings including fused, bridged, and spiro ring systems. When $C_y$ cycloalkyl or $C_{y-z}$ cycloalkyl is used, y and z indicate the number of carbon atoms in the ring assembly. One or more of the rings can be aryl, heteroaryl, or heterocyclic provided that the point of attachment is through the non-aromatic, non-heterocyclic ring carbocyclic ring. Examples of suitable cycloalkyl groups include, for instance, adamantyl, cyclopropyl, cyclobutyl, cyclopentyl, and cyclooctyl. Other examples of cycloalkyl groups include bicycle[2,2,2,]octanyl, norbornyl, and spirobicyclo groups such as spiro[4.5]dec-8-yl:

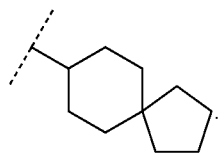

"Halo" or "halogen" refers to fluoro, chloro, bromo and iodo and preferably is fluoro, chloro or bromo.

"Haloalkyl" refers to alkyl groups substituted with 1 to 5, 1 to 3, or 1 to 2 halo groups, wherein alkyl and halo are as defined herein.

"Hydroxy" or "hydroxyl" refers to the group —OH.

"Heteroaryl" refers to an aromatic group of from 1 to 10 carbon atoms and 1 to 4 heteroatoms selected from the group consisting of oxygen, nitrogen and sulfur within the ring. Such heteroaryl groups can have a single ring (e.g., pyridinyl or furyl) or multiple condensed rings (e.g., indolizinyl or benzothienyl) wherein the condensed rings may or may not be aromatic and/or contain a heteroatom provided that the point of attachment is through an atom of the aromatic heteroaryl group. In one embodiment, the nitrogen and/or the sulfur ring atom(s) of the heteroaryl group are optionally oxidized to provide for the N-oxide (N→O), sulfinyl, and/or sulfonyl moieties. Preferred heteroaryls include pyridyl, pyrrolyl, indolyl, thiophenyl, and furanyl.

The term "x-membered heteroaryl" refers to a heteroaryl group having "x" ring atoms including carbon and heteroatoms.

"Nitrogen-containing heteroaryl" refers to a heteroaryl having at least one ring nitrogen atom.

"Heterocycle" or "heterocyclic" or "heterocycloalkyl" or "heterocyclyl" refers to a saturated or partially saturated, but not aromatic, group having from 1 to 10 ring carbon atoms and from 1 to 4 ring heteroatoms selected from the group consisting of nitrogen, sulfur, or oxygen. Heterocycle encompasses single ring or multiple condensed rings, including fused bridged and spiro ring systems. In fused ring systems, one or more the rings can be cycloalkyl, aryl, or heteroaryl provided that the point of attachment is through the non-aromatic heterocyclic ring. In one embodiment, the nitrogen and/or sulfur atom(s) of the heterocyclic group are optionally oxidized to provide for the N-oxide, sulfinyl, and/or sulfonyl moieties. The term "x-membered heterocycloalkyl" refers to a heterocycloalkyl group having "x" ring atoms including carbon and heteroatoms.

"Nitrogen-containing heterocycloalkyl" refers to a heterocycloalkyl having at least one ring nitrogen atom.

Examples of heterocycles and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), 1,1-dioxothiomorpholine, piperidine, pyrrolidine, and tetrahydrofuran.

"Nitro" refers to the group —$NO_2$.

"Oxo" refers to the atom (=O) or (—$O^-$).

"Alkylthio" refers to the group —S-alkyl wherein alkyl is as defined herein.

"⁓" represents the point of connection to the reminder of the molecule or the part of the molecule as specified.

"----" represents the point of connection to the reminder of the molecule or the part of the molecule as specified.

It is understood that chemically impermissible structures and substitution patterns (e.g., methyl substituted with 5 fluoro groups) are not contemplated by this application. Such impermissible structures and substitution patterns are well known to the skilled artisan.

"Compound" or "compounds" as used herein is meant to include the racemates, stereoisomers and tautomers of the indicated formulas unless otherwise specified.

"Stereoisomer" or "stereoisomers" include enantiomers and diastereomers and trans- and cis-isomers where applicable. Enantiomers and diastereomers are compounds that differ in the chirality of one or more stereocenters.

"Racemates" refers to a mixture of enantiomers.

"Tautomer" refer to alternate forms of a compound that differ in the position of a proton, such as enol-keto and imine-enamine tautomers, or the tautomeric forms of heteroaryl groups containing a ring atom attached to both a ring —NH— moiety and a ring =N— moiety such as pyrazoles, imidazoles, benzimidazoles, triazoles, and tetrazoles.

"Patient" refers to mammals and includes humans and non-human mammals.

"Salt" refers to a chemical entity formed between a compound and a counter ion from an acid or a base. "Pharmaceutically acceptable salt" refers to a salt of a compound that is derived from a variety of physiologically acceptable organic and inorganic counter ions. Such counter ions are well known in the art and include, by way of example only, sodium, potassium, calcium, magnesium, ammonium, aluminum, lithium and ammonium, for example tetraalkylammonium, and the like when the molecule contains an acidic functionality; and when the molecule contains a basic functionality, salts of organic or inorganic acids, such as hydrochloride, sulfate, phosphate, diphosphate, nitrate hydrobromide, tartrate, mesylate, acetate, malate, maleate, fumarate, tartrate, succinate, citrate, lactate, pamoate, salicylate, stearat, methanesulfonate, p-toluenesulfonate, thiocyanate, 1-hydroxy-2-naphthoate and oxalate, and the like. Suitable pharmaceutically acceptable salts also include those listed in Remington's Pharmaceutical Sciences, 17th Edition, pg. 1418 (1985) and P. Heinrich Stahl, Camille G. Wermuth (Eds.), Handbook of Pharmaceutical Salts Properties, Selection, and Use; 2002. Examples of acid addition salts include those formed from acids such as hydroiodic, phosphoric, metaphosphoric, nitric and sulfuric acids, and with organic acids, such as alginic, ascorbic, anthranilic, benzoic, camphorsulfuric, citric, embonic (pamoic), ethanesulfonic, formic, fumaric, furoic, galacturonic, gentisic, gluconic, glucuronic, glutamic, glycolic, isonicotinic, isothionic, lactic, malic, mandelic, methanesulfonic, mucic, pantothenic, phenylacetic, propionic, saccharic, salicylic, stearic, succinic, sulfinilic, trifluoroacetic and arylsulfonic for example benzenesulfonic and p-toluenesulfonic acids. Examples of base addition salts formed with alkali metals and alkaline earth metals and organic bases include chloroprocaine, choline, N,N-dibenzylethylenediamine, diethanolamine, ethylenediamine, lysine, meglumaine (N-methylglucamine), and procaine, as well as internally formed salts.

Salts having a non-physiologically acceptable anion or cation are within the scope of the invention as useful intermediates for the preparation of physiologically acceptable salts and/or for use in non-therapeutic, for example, in vitro, situations. A salt of the compounds prepared by this invention includes all structural variations due to the position of the salt proton unless otherwise indicated.

"Crystalline" refers to a material that contains a specific compound or a salt of the compound, which may be hydrated and/or solvated, and has sufficient crystalline content to exhibit a discernable diffraction pattern by XRPD or other diffraction techniques. In some cases, a crystalline material that is obtained by direct crystallization of a compound dissolved in a solvent or solvent mixture or solution or interconversion of crystals obtained under different crystallization conditions, may have crystals that contain the solvent used in the crystallization. Such compositions may be referred to as a crystalline solvate. Also, the specific solvent system and physical embodiment in which the crystallization is performed, collectively termed as crystallization conditions, may result in the crystalline material having physical and chemical properties that are unique to the crystallization conditions. This may be due to the orientation of the chemical moieties of the compound with respect to each other within the crystal and/or the predominance of a specific polymorphic or pseudopolymorphic form of the compound in the crystalline material. General methods for precipitating and crystallizing a compound may be applied to prepare the various polymorphs or pseudopolymorphs described herein. These general methods are known to one skilled in the art of synthetic organic chemistry and pharmaceutical formulation, and are described, for example, by J. March, "Advanced Organic Chemistry: Reactions, Mechanisms and Structure," 4th Ed. (New York: Wiley-InterScience, 1992) and *Remington: The Science and Practice of Pharmacy*, A. Gennaro, ed., 21st edition, -Lippincott, Williams & Wilkins, Philadelphia, Pa., 2006.

"Polymorph" or "polymorphic form" refers to a crystalline form of a substance that is distinct from another crystalline form but that shares the same chemical formula.

"Pseudopolymorph" refers to a crystalline form of a hydrate or solvate of a compound. In contrast to polymorphs, pseudopolymorphs are chemically identical except differ in the amount of water or solvent bound in the crystal lattice. Depending on the solvent used during synthesis and/or crystallization some compounds form hydrates (with water) or solvates (with other solvents) in different stoichiometric ratio. Pseudopolymorphs may show different physical properties like habitus, stability, dissolution rate and bioavailability as known for polymorphs.

"Solvent" refers to a liquid that dissolves a solid, liquid, or gaseous solute to form a solution. Common solvents are well known in the art and include but are not limited to, water; saturated aliphatic hydrocarbons, such as pentane, hexane, heptanes, and other light petroleum; aromatic hydrocarbons, such as benzene, toluene, xylene, etc.; halogenated hydrocarbons, such as dichloromethane, chloroform, carbon tetrachloride, etc.; aliphatic alcohols, such as methanol, ethanol, propanol, etc., ethers, such as diethyl ether, dipropyl ether, dibutyl ether, tetrahydrofuran, dioxane, etc.; ketones, such as acetone, ethyl methyl ketone, etc.; esters, such as methyl acetate, ethyl acetate, etc.; nitrogen-containing solvents, such as formamide, N,N-dimethylformamide, acetonitrile, pyridine, N-methylpyrrolidone, quinoline, nitrobenzene, etc.; sulfur-containing solvents, such as carbon disulfide, dimethyl sulfoxide, sulfolane, etc.; phosphorus-containing solvents, such as hexamethylphosphoric triamide, etc. The term solvent includes a combination of two or more solvents unless clearly indicated otherwise. A particular choice of a suitable solvent will depend on many factors, including the nature of the solvent and the solute to be dissolved and the intended purpose, for example, what chemical reactions will occur in the solution, and is generally known in the art.

"Base" generally refers to chemical compounds that can accept hydrogen ions. The term "inorganic base" refers to an inorganic compound that can act as a base. Examples of inorganic base include, but are not limited to, sodium carbonate, potassium hydroxide (KOH), barium hydroxide ($Ba(OH)_2$), cesium hydroxide (CsOH), sodium hydroxide (NaOH), strontium hydroxide ($Sr(OH)_2$), calcium hydroxide ($Ca(OH)_2$), lithium hydroxide (LiOH), rubidium hydroxide (RbOH), and magnesium hydroxide ($Mg(OH)_2$). The term "organic base" refers to an organic compound that can act as a base. Examples of inorganic base include, but are not limited to, triethylamine, N-methylmorpholine, diisopropylethylamine, pyridine and 4-dimethylaminopyridine (DMAP).

"Acid" refers to a chemical species that can either donate a proton or accept a pair of electrons from another species. Examples of acids include organic acids, such as carboxylic acids (e.g. maleic acid, lactic acid, acetic acid, formic acid, citric acid, oxalic acid, uric acid, etc.) and sulfonic acids (e.g., methanesulfonic acid, p-toluenesulfonic acid); mineral acids (e.g. hydrochloric acid, nitric acid, phosphoric acid, sulfuric acid, boric acid, hydrofluoric acid, hydrobromic acid); and Lewis acids.

"Lewis acid" refers to a chemical compound that is an electron pair acceptor. Non-limiting examples of Lewis acids include proton ($H^+$), diborane ($B_2H_6$), boron trifluoride ($BF_3$), aluminum chloride ($AlCl_3$), aluminum fluoride ($AlF_3$), silicon tetrafluoride ($SiF_4$), phosphorus pentachloride ($PCl_5$), sulfur tetrafluoride ($SF_4$), tin(IV) chloride ($SnCl_4$), etc.

"Contacting" refers to bringing two or more chemical molecules to close proximity so that a reaction between the two or more chemical molecules can occur. For example, contacting may comprise mixing and optionally continuously mixing the chemicals. Contacting may be done by fully or partially dissolving or suspending two or more chemicals in one or more solvents, mixing of a chemical in a solvent with another chemical in solid and/or gas phase or being attached on a solid support, such as a resin, or mixing two or more chemicals in gas or solid phase and/or on a solid support, that are generally known to those skilled in the art.

"Converting" refers to the process of changing one chemical compound to another chemical compound via a chemical reaction, or changing a free acid or base of a chemical compound to a salt of the compound, or changing one salt of a chemical compound to another salt of the chemical compound under reaction conditions capable of bringing about the change.

The term "reaction conditions" refers to the details under which a chemical reaction proceeds. Examples of reaction conditions include, but are not limited to, one or more of following: reaction temperature, solvent, pH, pressure, reaction time, mole ratio of reactants, the presence of a base or acid, or catalyst, etc. Reaction conditions may be named after the particular chemical reaction in which the conditions are employed, such as, coupling conditions, hydrogenation conditions, acylation conditions, reduction conditions, salt forming conditions, etc. Reaction conditions for known reactions are generally known to those skilled in the art.

The term "salt formation conditions" or "salt forming conditions" generally refers to conditions used to form a salt between, for example, a compound having a basic group, such as a compound of Formula I with an organic or inorganic acid. Salt forming conditions may include mixing the molecule having the basic group and the acid in a solvent or a mixture of solvents for a period of time under a certain temperature, which would be generally known to a person skilled in the art. Alternatively, the compound can be passed over an ion exchange resin to form the desired salt or one salt form of the product can be converted into another using the same general process. The first salt can then be converted to a second salt such as a maleate salt. Salt forming conditions may also be conditions where the acid is a by-product of a reaction forming the compound whose salt is formed.

The term "reducing agent" generally refers to a chemical substance that when reacts with another chemical compound, can convert the other compound to a different compound with additional hydrogen atom(s). For example, certain reducing agents can convert a compound with a group —CH=N— to a compound with a group —$CH_2$—NH— by adding two hydrogen atoms to the compound with the group —CH=N—. Examples of such reducing agents are generally known to those skilled in the art and include but are not limited to hydrogen (which usually acts in the presence of a catalyst, such as Raney nickel or palladium on activated carbon), lithium tetrahydridoaluminate(III) (lithium aluminium hydride), sodium tetrahydridoborate(III) (sodium borohydride), trialkylsilane, phenylsilane, trichlorosilane, polymethylhydrosiloxane, and tris(trimethylsilyl)silane.

"Trialkylsilane" refers to a compound which is of the formula $R^f_3SiH$, wherein each $R^f$ is independently $C_{1-4}$ alkyl. Non-limiting examples of trialkylsilane include trimethylsilane and triethylsilane.

"Elevated temperature" refers to a temperature that is above ambient temperature.

The term "coupling conditions" generally refers to conditions used in coupling reactions where two chemical entities are connected to form one chemical entity via a coupling reagent.

The term "isolating conditions" or "isolation conditions" generally refers to conditions used to separate a compound or a salt or a solvate thereof from a mixture in a substantially pure form. In some embodiments, the purity of the isolated compound or a salt or a solvate thereof has a purity of at least about 85%, preferably at least about 90%, more preferably at least about 95%, or about 98%. Common isolation techniques include extraction, evaporation of solvent, crystallization, recrystallization, filtration, separation by chromatography, such as liquid or gas chromatography, etc, which are generally known to those skilled in the art. Specific techniques and conditions in isolating a particular compound or a salt or a solvate thereof vary depending on many factors including the nature of the mixture, the property of the compound or a salt or a solvate thereof, quantity to be isolated, and the desired purity, etc.

"Catalyst" refers to a chemical substance which, when used in certain chemical reactions, increases the rate of the chemical reaction or makes the chemical reactions proceed in a practical manner. A catalyst itself is not consumed by the reaction. Many suitable catalysts are generally known for many reactions. New catalysts for known reactions or for new reactions have been emerging with the advance of the chemical science. As used herein, all suitable catalysts are encompassed unless specifically indicated otherwise.

It is to be understood that when a value is recited for a condition or a yield, the value may vary within a reasonable range, such as ±10%, ±5%, and ±1%. Similarly, the term "about" when used before a numerical value indicates that the value may vary within reasonable range, such as ±10%, ±5%, and ±1%.

The term "compound of Formula III" and "Compound III" are used interchangeably to refer to the compound 5-chloro-N-((1-(4-(2-oxopyridin-1(2H)-yl)phenyl)-1H-imidazol-4-yl)methyl)thiophene-2-carboxamide, having the structure:

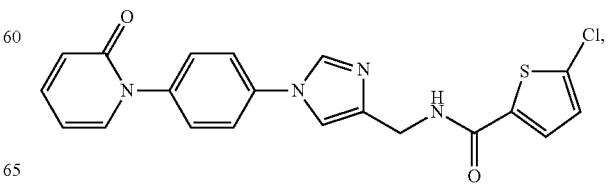

or tautomer thereof, which is described in U.S. Pat. Nos. 7,763,608 and 7,767,697, which are hereby incorporated by reference in their entirety.

"The mesylate salt of the compound of Formula III" and "the mesylate salt of Compound III" are used interchangeably to describe the salt formed between Compound III, (5-chloro-N-((1-(4-(2-oxopyridin-1(2H)-yl)phenyl)-1H-imidazol-4-yl)methyl)thiophene-2-carboxamide), and methanesulfonic acid ($CH_3SO_3H$), preferably in a ratio of about 1 to 1.

In some embodiments, the mesylate salt of Compound III is of the formula:

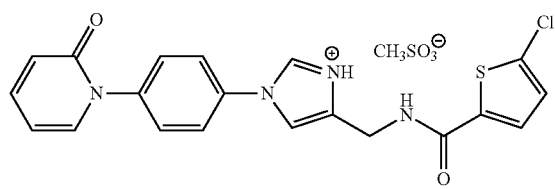 [SMILES: O=C(NCc1cn(-c2ccc(-n3ccccc3=O)cc2)c[nH+]1)c1ccc(Cl)s1 ; "CH3SO3"]

Synthetic Methods

Various synthetic methods for preparing a compound of Formula I, II or III have been reported, see for example, U.S. Pat. No. 7,521,470 (the '470 patent), U.S. Pat. Nos. 7,696,352, 7,763,608, and U.S. Patent Application Publication Nos. 2008/0293704 and 2008/0051578. The methods of the present invention significantly simplify the synthesis as compared with those reported methods. For example, U.S. Pat. No. 7,521,470 describes a procedure for preparing a compound, 5-chloro-N-((5-methyl-1-(4-(2-oxopyridin-1(2H)-yl)phenyl)-1H-imidazol-4-yl)methyl)thiophene-2-carboxamide as shown in the Comparison Scheme.

Comparison Scheme

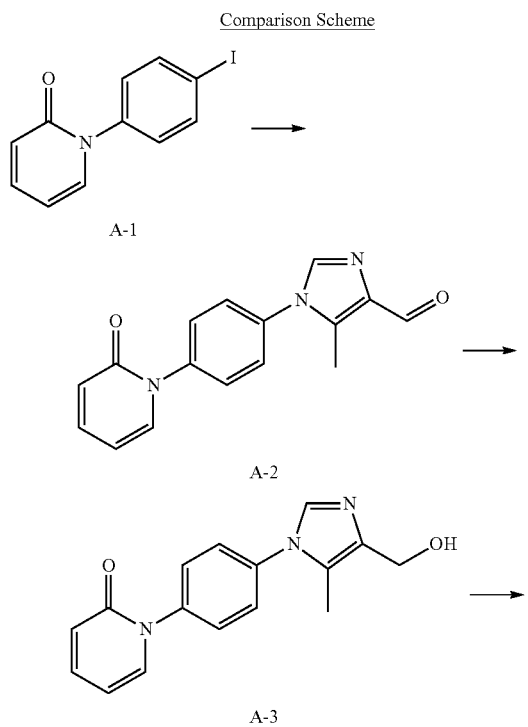

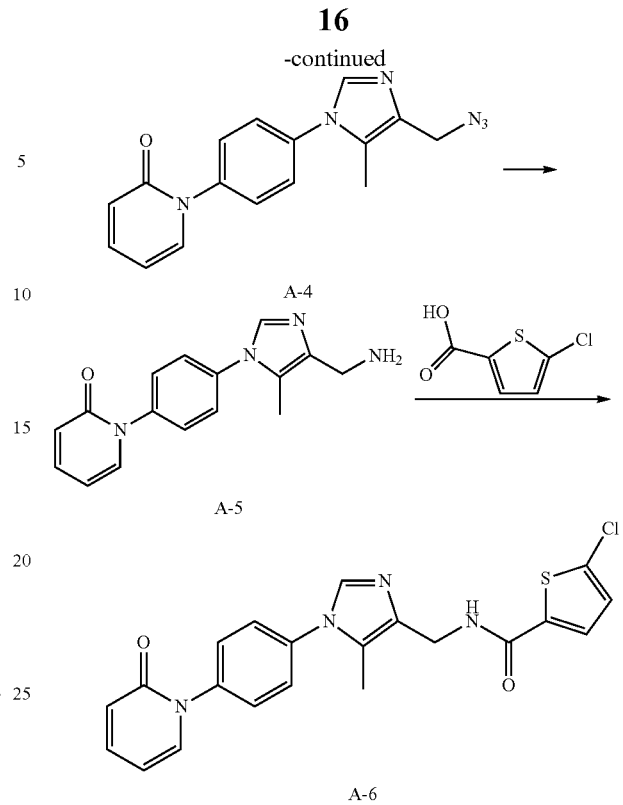

In the above method described in the '470 patent, the aldehyde compound A-2 was converted the amino compound A-5 via the alcohol compound A-3 and the azide compound A-4 by a three-step procedure before it was coupled with 5-chlorothiophene-2-carboxylic acid in the presence of an amide coupling agent N-[(dimethylamino)-1H-1,2,3-triazolo[4,5-b]pyridine-1-ylmethylene]-N-methylmethanaminium hexafluorophosphate N-oxide (HATU). Alternatively, compound A-2 may be converted to compound A-5 by a reductive amination reaction using a reducing agent, such as the commonly used sodium borohydride.

The methods of the present invention allow the aldehyde compound of formula I-A to be coupled to the amide compound of Formula I-B in a one-step process eliminating the need of using agents, such as sodium borohydride and/or an amide coupling agent, such as HATU, which are expensive or produce by-products that are difficult to separate from the desired product. The methods of this invention are particularly advantageous for large scale syntheses. Further, overall yield is improved from about 3.5% to about 11.1%.

In one aspect, the invention is directed to methods of preparing a compound of Formula I or a salt thereof or a hydrate of the compound or salt thereof:

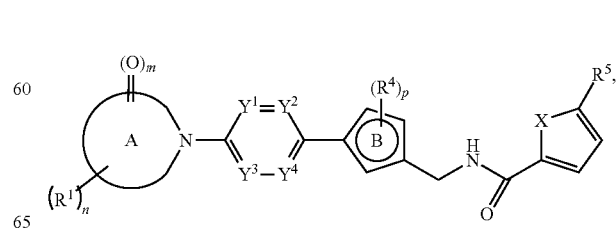

comprising contacting a compound of formula I-A

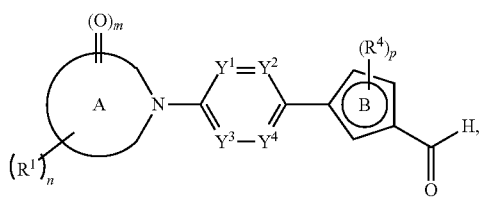

with a compound of formula I-B

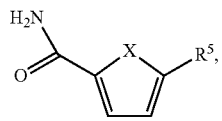

under reaction conditions to form the compound of formula I or the salt or the hydrate; and wherein:

ring A is 5-, 6-, or 7-membered nitrogen-containing heterocycloalkyl or 5-, 6-, or 7-membered nitrogen-containing heteroaryl;

ring B is a 5-membered nitrogen-containing heteroaryl;

$Y^1$, $Y^2$, $Y^3$, and $Y^4$ are independently $CR^2$ or N provided that at least two of $Y^1$, $Y^2$, $Y^3$, and $Y^4$ are $CR^2$;

each $R^1$ is independently selected from the group consisting of $C_{1-8}$ alkyl, halo, nitro, cyano, $OR^{12}$, $SR^{12}$, $S(O)R^{12}$, $S(O)_2R^{12}$, $C(O)R^{12}$, $OC(O)R^{12}$, $OC(O)NHR^{12}$, $CO_2R^{12}$, $NHS(O)_2R^{12}$, $S(O)_2NHR^{12}$, $NHC(O)NHR^{12}$, $C(O)NHR^{12}$, $NHC(O)R^{12}$, $NHC(O)OR^{12}$, aryl, heteroaryl and heterocycloalkyl, wherein each of the $C_{1-8}$ alkyl, aryl, heteroaryl and heterocycloalkyl are optionally substituted with 1 to 3 $R^{11}$;

each $R^2$ is independently selected from the group consisting of hydrogen, $C_{1-8}$ alkyl, halo, nitro, cyano, $OR^{12}$, $SR^{12}$, $S(O)R^{12}$, $S(O)_2R^{12}$, $NHS(O)_2R^{12}$, $S(O)_2NHR^{12}$, $S(O)_2NR^{12}R^{12}$, $NHC(O)NHR^{12}$, $NHC(O)NR^{12}R^{12}$, $C(O)NHR^{12}$, $C(O)NR^{12}R^{12}$, $C(O)R^{12}$, $OC(O)R^{12}$, $OC(O)NHR^{12}$, $OC(O)NR^{12}R^{12}$, $CO_2R^{12}$, $NHC(O)R^{12}$, $NHC(O)OR^{12}$, aryl, heteroaryl and heterocycloalkyl, wherein each of the $C_{1-8}$ alkyl, aryl, heteroaryl and heterocycloalkyl are optionally substituted with 1 to 3 $R^{11}$;

$R^4$ is independently selected from the group consisting of alkyl, halo, hydroxy, $C_{1-4}$ alkoxy, $SR^{12}$, $S(O)R^{12}$, $S(O)_2R^{12}$, $C(O)R^{12}$, $OC(O)R^{12}$, $OC(O)NHR^{12}$, $CO_2R^{12}$, $NHS(O)_2R^{12}$, $S(O)_2NHR^{12}$, $NHC(O)NHR^{12}$, $C(O)NHR^{12}$, $NHC(O)R^{12}$, $NHC(O)OR^{12}$, aryl, heteroaryl, and heterocycloalkyl, wherein the alkyl, aryl, heteroaryl, and heterocycloalkyl are optionally substituted with 1 to 3 $R^{11}$;

X is S or O;

$R^5$ is selected from the group consisting of halo, $C_{1-4}$ alkyl, $C_{2-4}$ alkenyl and $C_{2-4}$ alkynyl;

m is 0, 1, or 2;

n is 0, 1, 2, 3, or 4;

p is 0, 1, 2, or 3;

each $R^{11}$ is independently selected from the group consisting of halo, oxo, nitro, cyano, carboxyl, $C_{1-4}$ alkyl, $C_{1-4}$ haloalkyl, $OR^{12}$, $SR^{12}$, $S(O)R^{12}$, $S(O)_2R^{12}$, $NHS(O)_2R^{12}$, $S(O)_2NHR^{12}$, $S(O)_2NR^{12}R^{12}$, $C(O)R^{12}$, $OC(O)R^{12}$, $OC(O) NHR^{12}$, $OC(O)NR^{12}R^{12}$, $CO_2R^{12}$, $NHC(O)R^{12}$, $NHC(O) NHR^{12}$, $NHC(O)NR^{12}R^{12}$, $C(O)NHR^{12}$, $C(O)NR^{12}R^{12}$, $NHC(O)OR^{12}$, $C_{3-6}$ cycloalkyl, aryl, heterocycloalkyl, and heteroaryl, wherein the $C_{1-4}$ alkyl, heterocycloalkyl and heteroaryl are optionally substituted with 1 to 3 substituents independently selected from the group consisting of halo, nitro, cyano, $OR^{12}$, $SR^{12}$, $S(O)R^{12}$, $S(O)_2R^{12}$, $NHS(O)_2R^{12}$, $S(O)_2NHR^{12}$, $S(O)_2NR^{12}R^{12}$, $NHC(O)NHR^{12}$, $C(O)NHR^{12}$, $C(O)NR^{12}R^{12}$, $C(O)R^{12}$, $OC(O)R^{12}$, $OC(O)NHR^{12}$, $OC(O) NR^{12}R^{12}$, $CO_2R^{12}$, $NHC(O)R^{12}$, $NHC(O)OR^{12}$, $C_{1-4}$ alkyl, $C_{1-4}$ haloalkyl, hydroxy, $C_{1-4}$ alkoxy, $C_{3-6}$ cycloalkyl, heterocycloalkyl, aryl, and heteroaryl;

each $R^{12}$ is independently selected from the group consisting of alkyl, cycloalkyl, aryl, heteroaryl, and heterocycloalkyl, wherein the alkyl, cycloalkyl, aryl, heteroaryl, and heterocycloalkyl are optionally substituted with 1 to 3 substituents independently selected from the group consisting of halo, oxo, nitro, cyano, carboxyl, carboxyl ester, $C_{1-4}$ alkyl, $C_{1-4}$ haloalkyl, $OR^{13}$, $SR^{13}$, $S(O)R^{13}$, $S(O)_2R^{13}$, $NHS(O)_2 R^{13}$, $S(O)_2NHR^{13}$, $S(O)_2NR^{13}R^{13}$, $C(O)R^{13}$, $CO_2R^{13}$, $NHC (O)R^{13}$, $NHC(O)NHR^{13}$, $NHC(O)NR^{13}R^{13}$, $C(O)NHR^{13}$, $OC(O)NHR^{13}$, $OC(O)NR^{13}R^{13}$, $C(O)NR^{13}R^{13}$, $NHC(O) OR^{13}$, heterocycloalkyl, and heteroaryl; or two $R^{12}$ attached to the same nitrogen together with nitrogen attached thereto form a heterocycloalkyl optionally substituted with oxo or $C_{1-4}$ alkyl; and each $R^{13}$ is independently $C_{1-4}$ alkyl optionally substituted with from 1 to 2 substituents independently selected from the group consisting of halo, nitro, cyano, hydroxyl, alkoxy, carboxyl and carboxyl ester; or two $R^{13}$ attached to the same nitrogen together with nitrogen attached thereto form a heterocycloalkyl optionally substituted with oxo or $C_{1-4}$ alkyl.

In some embodiments, all of $Y^1$, $Y^2$, $Y^3$, and $Y^4$ are $CR^2$. In some embodiments, one of $Y^1$, $Y^2$, $Y^3$, and $Y^4$ is $CR^2$, wherein $R^2$ is not hydrogen, and the remaining of $Y^1$, $Y^2$, $Y^3$, and $Y^4$ are CH. In some embodiments, all of $Y^1$, $Y^2$, $Y^3$, and $Y^4$ are CH. In some embodiments, one of $Y^1$, $Y^2$, $Y^3$, and $Y^4$ is N, and the remaining of $Y^1$, $Y^2$, $Y^3$, and $Y^4$ are $CR^2$. In some embodiments, one of $Y^1$, $Y^2$, $Y^3$, and $Y^4$ is N, and the remaining of $Y^1$, $Y^2$, $Y^3$, and $Y^4$ are CH. In some embodiments, $Y^2$ is N, and $Y^1$, $Y^3$, and $Y^4$ are $CR^2$. In some embodiments, $Y^2$ is N, and $Y^1$, $Y^3$, and $Y^4$ are CH. In some embodiments, $Y^1$ is CF, and $Y^1$, $Y^3$, and $Y^4$ are CH. In some embodiments, $Y^2$ is CF, and $Y^1$, $Y^3$, and $Y^4$ are CH.

In some embodiments, the compound of Formula I is a compound of Formula Ia:

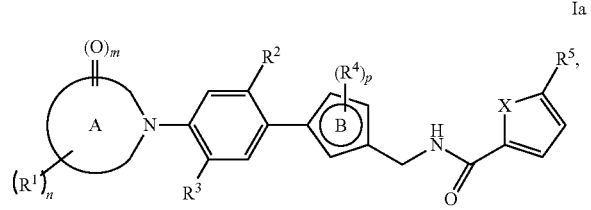

and the method comprises contacting a compound of formula I-Aa

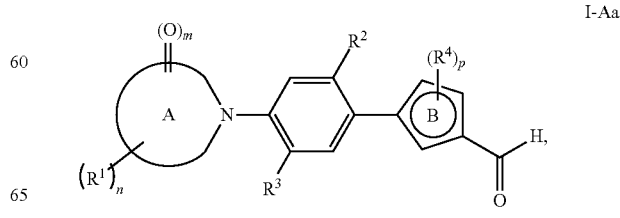

with a compound of formula I-B

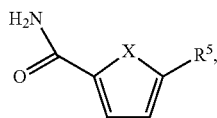

under reaction conditions to form the compound of formula Ia or the salt or the hydrate; and wherein:

ring A is 5-, 6-, or 7-membered nitrogen-containing heterocycloalkyl or 6-, 5-, or 7-membered nitrogen-containing heteroaryl;

ring B is a 5-membered nitrogen-containing heteroaryl;

each $R^1$ is independently selected from the group consisting of $C_{1-8}$ alkyl, halo, nitro, cyano, $OR^{12}$, $SR^{12}$, $S(O)R^{12}$, $S(O)_2R^{12}$, $C(O)R^{12}$, $OC(O)R^{12}$, $OC(O)NHR^{12}$, $CO_2R^{12}$, $NHS(O)_2R^{12}$, $S(O)_2NHR^{12}$, $NHC(O)NHR^{12}$, $C(O)NHR^{12}$, $NHC(O)R^{12}$, $NHC(O)OR^{12}$, aryl, heteroaryl and heterocycloalkyl, wherein each of the $C_{1-8}$ alkyl, aryl, heteroaryl and heterocycloalkyl are optionally substituted with 1 to 3 $R^{11}$;

$R^2$ and $R^3$ are independently selected from the group consisting of hydrogen, $C_{1-8}$ alkyl, halo, nitro, cyano, $OR^{12}$, $SR^{12}$, $S(O)R^{12}$, $S(O)_2R^{12}$, $NHS(O)_2R^{12}$, $S(O)_2NHR^{12}$, $S(O)_2NR^{12}R^{12}$, $NHC(O)NHR^{12}$, $NHC(O)NR^{12}R^{12}$, $C(O)NHR^{12}$, $C(O)NR^{12}R^{12}$, $C(O)R^{12}$, $OC(O)R^{12}$, $OC(O)NHR^{12}$, $OC(O)NR^{12}R^{12}$, $CO_2R^{12}$, $NHC(O)R^{12}$, $NHC(O)OR^{12}$, aryl, heteroaryl and heterocycloalkyl, wherein each of the $C_{1-8}$ alkyl, aryl, heteroaryl and heterocycloalkyl are optionally substituted with 1 to 3 $R^{11}$;

$R^4$ is independently selected from the group consisting of alkyl, halo, hydroxy, $C_{1-4}$ alkoxy, $SR^{12}$, $S(O)R^{12}$, $S(O)_2R^{12}$, $C(O)R^{12}$, $OC(O)R^{12}$, $OC(O)NHR^{12}$, $CO_2R^{12}$, $NHS(O)_2R^{12}$, $S(O)_2NHR^{12}$, $NHC(O)NHR^{12}$, $C(O)NHR^{12}$, $NHC(O)R^{12}$, $NHC(O)OR^{12}$, aryl, heteroaryl, and heterocycloalkyl, wherein the alkyl, aryl, heteroaryl, and heterocycloalkyl are optionally substituted with 1 to 3 $R^{11}$;

X is S or O;

$R^5$ is selected from the group consisting of halo, $C_{1-4}$ alkyl, $C_{2-4}$ alkenyl and $C_{2-4}$ alkynyl;

m is 0, 1, or 2;

n is 0, 1, 2, 3, or 4;

p is 0, 1, 2, or 3;

each $R^{11}$ is independently selected from the group consisting of halo, oxo, nitro, cyano, carboxyl, $C_{1-4}$ alkyl, $C_{1-4}$ haloalkyl, $OR^{12}$, $SR^{12}$, $S(O)R^{12}$, $S(O)_2R^{12}$, $NHS(O)_2R^{12}$, $S(O)_2NHR^{12}$, $S(O)_2NR^{12}R^{12}$, $C(O)R^{12}$, $OC(O)R^{12}$, $OC(O)NHR^{12}$, $OC(O)NR^{12}R^{12}$, $CO_2R^{12}$, $NHC(O)R^{12}$, $NHC(O)NHR^{12}$, $NHC(O)NR^{12}R^{12}$, $C(O)NHR^{12}$, $C(O)NR^{12}R^{12}$, $NHC(O)OR^{12}$, $C_{3-6}$ cycloalkyl, aryl, heterocycloalkyl, and heteroaryl, wherein the $C_{1-4}$ alkyl, heterocycloalkyl and heteroaryl are optionally substituted with 1 to 3 substituents independently selected from the group consisting of halo, nitro, cyano, $OR^{12}$, $SR^{12}$, $S(O)R^{12}$, $S(O)_2R^{12}$, $NHS(O)_2R^{12}$, $S(O)_2NHR^{12}$, $S(O)_2NR^{12}R^{12}$, $NHC(O)NHR^{12}$, $C(O)NHR^{12}$, $C(O)NR^{12}R^{12}$, $C(O)R^{12}$, $OC(O)R^{12}$, $OC(O)NHR^{12}$, $OC(O)NR^{12}R^{12}$, $CO_2R^{12}$, $NHC(O)R^{12}$, $NHC(O)OR^{12}$, $C_{1-4}$ alkyl, $C_{1-4}$ haloalkyl, hydroxy, $C_{1-4}$ alkoxy, $C_{3-6}$ cycloalkyl, heterocycloalkyl, aryl, and heteroaryl;

each $R^{12}$ is independently selected from the group consisting of alkyl, cycloalkyl, aryl, heteroaryl, and heterocycloalkyl, wherein the alkyl, cycloalkyl, aryl, heteroaryl, and heterocycloalkyl are optionally substituted with 1 to 3 substituents independently selected from the group consisting of halo, oxo, nitro, cyano, carboxyl, carboxyl ester, $C_{1-4}$ alkyl, $C_{1-4}$ haloalkyl, $OR^{13}$, $SR^{13}$, $S(O)R^{13}$, $S(O)_2R^{13}$, $NHS(O)_2R^{13}$, $S(O)_2NHR^{13}$, $S(O)_2NR^{13}R^{13}$, $C(O)R^{13}$, $CO_2R^{13}$, $NHC(O)R^{13}$, $NHC(O)NHR^{13}$, $NHC(O)NR^{13}R^{13}$, $C(O)NHR^{13}$, $OC(O)NHR^{13}$, $OC(O)NR^{13}R^{13}$, $C(O)NR^{13}R^{13}$, $NHC(O)OR^{13}$, heterocycloalkyl, and heteroaryl; or two $R^{12}$ attached to the same nitrogen together with nitrogen attached thereto form a heterocycloalkyl optionally substituted with oxo or $C_{1-4}$ alkyl; and each $R^{13}$ is independently $C_{1-4}$ alkyl optionally substituted with from 1 to 2 substituents independently selected from the group consisting of halo, nitro, cyano, hydroxyl, alkoxy, carboxyl and carboxyl ester; or two $R^{13}$ attached to the same nitrogen together with nitrogen attached thereto form a heterocycloalkyl optionally substituted with oxo or $C_{1-4}$ alkyl.

In some embodiments, the group

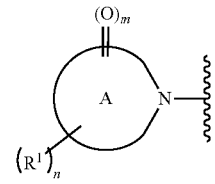

is selected from the group consisting of

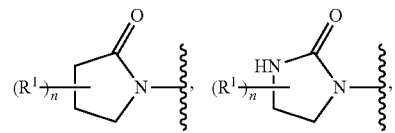

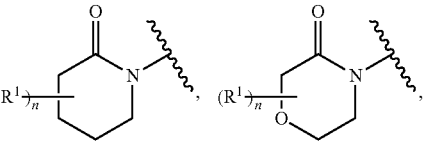

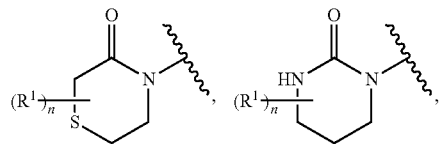

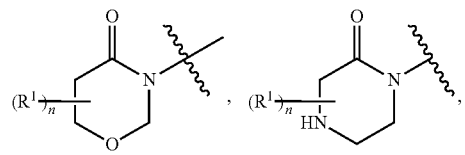

-continued

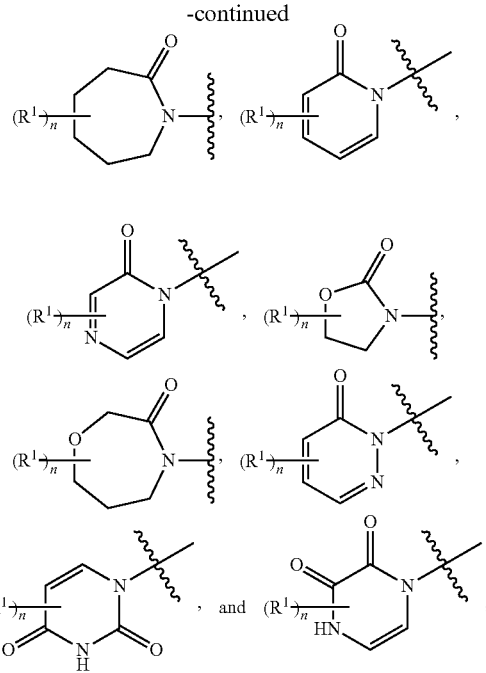

wherein $R^1$ can be at any position suitable for a substituent, and if $R^1$ is attached to a nitrogen atom, then it replaces the hydrogen atom attached thereto; and
"⁓" represents the point of connection to the rest of the molecule.

In some embodiments, the nitrogen atom(s) in ring A is substituted with $R^1$.

In some embodiments, the group

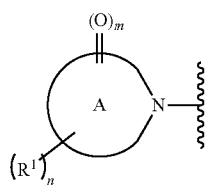

is selected from the group consisting of

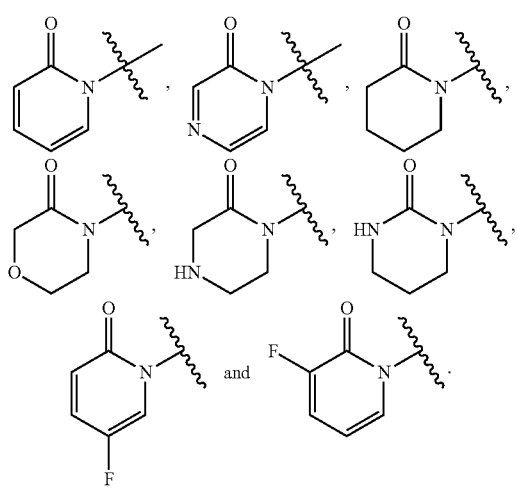

In another aspect, this invention provides a method of preparing a compound of Formula II or a salt thereof or a hydrate of the compound or the salt thereof:

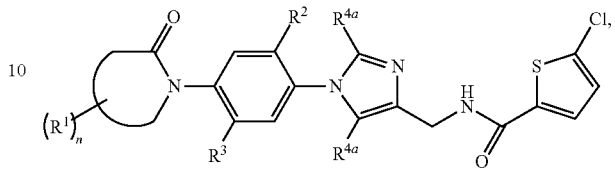

II comprising contacting a compound of Formula II-A

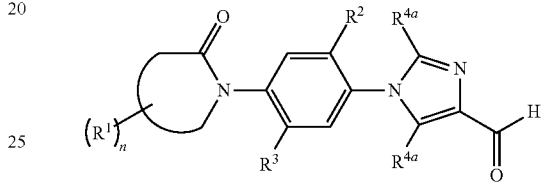

II-A with a compound of Formula II-B

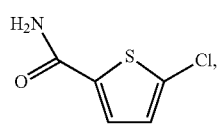

II-B under reaction conditions to form the compound of Formula II or the salt or the hydrate; and
wherein:
the group

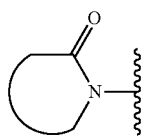 [SMILES: *N(C)C(C)=O]

is selected from the group consisting of:

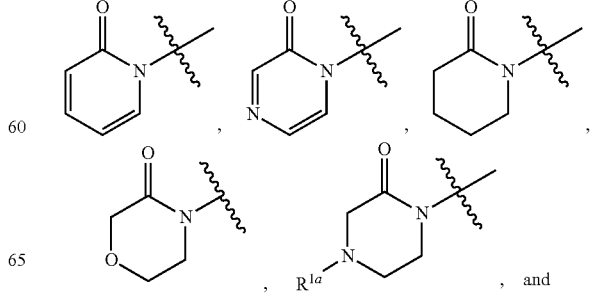

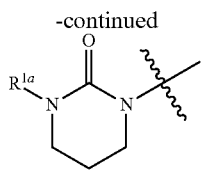

$R^{1a}$ is hydrogen or $R^1$;

each $R^1$ is independently selected from the group consisting of $C_{1-8}$ alkyl, halo, nitro, cyano, $OR^{12}$, $SR^{12}$, $S(O)R^{12}$, $S(O)_2R^{12}$, $C(O)R^{12}$, $OC(O)R^{12}$, $OC(O)NHR^{12}$, $CO_2R^{12}$, $NHS(O)_2R^{12}$, $S(O)_2NHR^{12}$, $NHC(O)NHR^{12}$, $C(O)NHR^{12}$, $NHC(O)R^{12}$, $NHC(O)OR^{12}$, aryl, heteroaryl and heterocycloalkyl, wherein each of the $C_{1-8}$ g alkyl, aryl, heteroaryl and heterocycloalkyl are optionally substituted with 1 to 3 $R^{11}$;

$R^2$ and $R^3$ are independently selected from the group consisting of hydrogen, $C_{1-8}$ alkyl, halo, nitro, cyano, $OR^{12}$, $SR^{12}$, $S(O)R^{12}$, $S(O)_2R^{12}$, $NHS(O)_2R^{12}$, $S(O)_2NHR^{12}$, $S(O)_2NR^{12}R^{12}$, $NHC(O)NHR^{12}$, $NHC(O)NR^{12}R^{12}$, $C(O)NHR^{12}$, $C(O)NR^{12}R^{12}$, $C(O)R^{12}$, $OC(O)R^{12}$, $OC(O)NHR^{12}$, $OC(O)NR^{12}R^{12}$, $CO_2R^{12}$, $NHC(O)R^{12}$, $NHC(O)OR^{12}$, aryl, heteroaryl and heterocycloalkyl, wherein each of the $C_{1-8}$ alkyl, aryl, heteroaryl and heterocycloalkyl are optionally substituted with 1 to 3 $R^{11}$;

each $R^{4a}$ is independently hydrogen or $R^4$; $R^4$ is independently selected from the group consisting of alkyl, halo, hydroxy, $C_{1-4}$ alkoxy, $SR^{12}$, $S(O)R^{12}$, $S(O)_2R^{12}$, $C(O)R^{12}$, $OC(O)R^{12}$, $OC(O)NHR^{12}$, $CO_2R^{12}$, $NHS(O)_2R^{12}$, $S(O)_2NHR^{12}$, $NHC(O)NHR^{12}$, $C(O)NHR^{12}$, $NHC(O)R^{12}$, $NHC(O)OR^{12}$, aryl, heteroaryl, and heterocycloalkyl, wherein the alkyl, aryl, heteroaryl, and heterocycloalkyl are optionally substituted with 1 to 3 $R^{11}$;

each $R^{11}$ is independently selected from the group consisting of halo, oxo, nitro, cyano, carboxyl, carboxyl ester, $C_{1-4}$ alkyl, $C_{1-4}$ haloalkyl, $OR^{12}$, $SR^{12}$, $S(O)R^{12}$, $S(O)_2R^{12}$, $NHS(O)_2R^{12}$, $S(O)_2NHR^{12}$, $S(O)_2NR^{12}R^{12}$, $C(O)R^{12}$, $OC(O)R^{12}$, $OC(O)NHR^{12}$, $OC(O)NR^{12}R^{12}$, $CO_2R^{12}$, $NHC(O)R^{12}$, $NHC(O)NHR^{12}$, $NHC(O)NR^{12}R^{12}$, $C(O)NHR^{12}$, $C(O)NR^{12}R^{12}$, $NHC(O)OR^{12}$, $C_{3-6}$ cycloalkyl, aryl, heterocycloalkyl, and heteroaryl, wherein the $C_{1-4}$ alkyl, heterocycloalkyl and heteroaryl are optionally substituted with 1 to 3 substituents independently selected from the group consisting of halo, nitro, cyano, $OR^{12}$, $SR^{12}$, $S(O)R^{12}$, $S(O)_2R^{12}$, $NHS(O)_2R^{12}$, $S(O)_2NHR^{12}$, $S(O)_2NR^{12}R^{12}$, $NHC(O)NHR^{12}$, $C(O)NHR^{12}$, $C(O)NR^{12}R^{12}$, $C(O)R^{12}$, $OC(O)R^{12}$, $OC(O)NHR^{12}$, $OC(O)NR^{12}R^{12}$, $CO_2R^{12}$, $NHC(O)R^{12}$, $NHC(O)OR^{12}$, $C_{1-4}$ alkyl, $C_{1-4}$ haloalkyl, hydroxy, $C_{1-4}$ alkoxy, $C_{3-6}$ cycloalkyl, heterocycloalkyl, aryl, and heteroaryl;

$R^{12}$ is selected from the group consisting of alkyl, cycloalkyl, aryl, heteroaryl, and heterocycloalkyl, wherein the alkyl, cycloalkyl, aryl, heteroaryl, and heterocycloalkyl are optionally substituted with 1 to 3 substituents independently selected from the group consisting of halo, oxo, nitro, cyano, carboxyl, carboxyl ester, $C_{1-4}$ alkyl, $C_{1-4}$ haloalkyl, $OR^{13}$, $SR^{13}$, $S(O)R^{13}$, $S(O)_2R^{13}$, $NHS(O)_2R^{13}$, $S(O)_2NHR^{13}$, $S(O)_2NR^{13}R^{13}$, $C(O)R^{13}$, $CO_2R^{13}$, $NHC(O)R^{13}$, $NHC(O)NHR^{13}$, $NHC(O)NR^{13}R^{13}$, $C(O)NHR^{13}$, $OC(O)NHR^{13}$, $OC(O)NR^{13}R^{13}$, $C(O)NR^{13}R^{13}$, $NHC(O)OR^{13}$, heterocycloalkyl, and heteroaryl; or two $R^{12}$ attached to the same nitrogen together with nitrogen attached thereto form a heterocycloalkyl optionally substituted with oxo or $C_{1-4}$ alkyl;

each $R^{13}$ is independently $C_{1-4}$ alkyl optionally substituted with from 1 to 2 substituents independently selected from the group consisting of halo, nitro, cyano, hydroxyl, alkoxy, carboxyl and carboxyl ester; or two $R^{13}$ attached to the same nitrogen together with nitrogen attached thereto form a heterocycloalkyl optionally substituted with oxo or $C_{1-4}$ alkyl; and n is 0, 1, 2, 3, or 4, provided that when $R^{1a}$ is not hydrogen, then n is 0, 1, 2, or 3.

In some embodiments, n is 0. In some embodiments, n is 1.

In some embodiments, the group

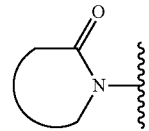

is selected from the group consisting of:

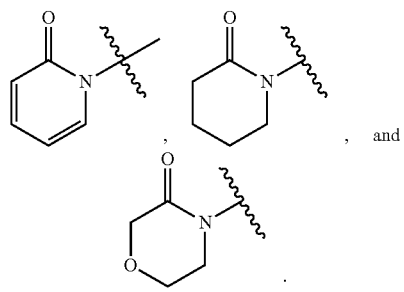

, and

In some embodiments, the group

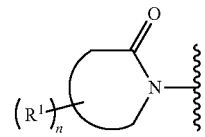

is selected from the group consisting of

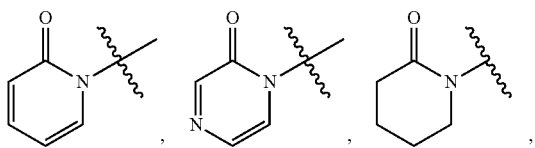

,

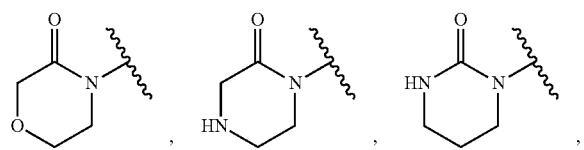

,

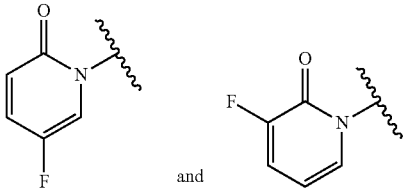

and

In some embodiments, $R^{1a}$ is $R^1$.

In some embodiments, ring B is a nitrogen-containing heteroaryl. In some embodiments, the group

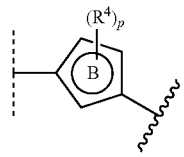

is selected from the group consisting of:

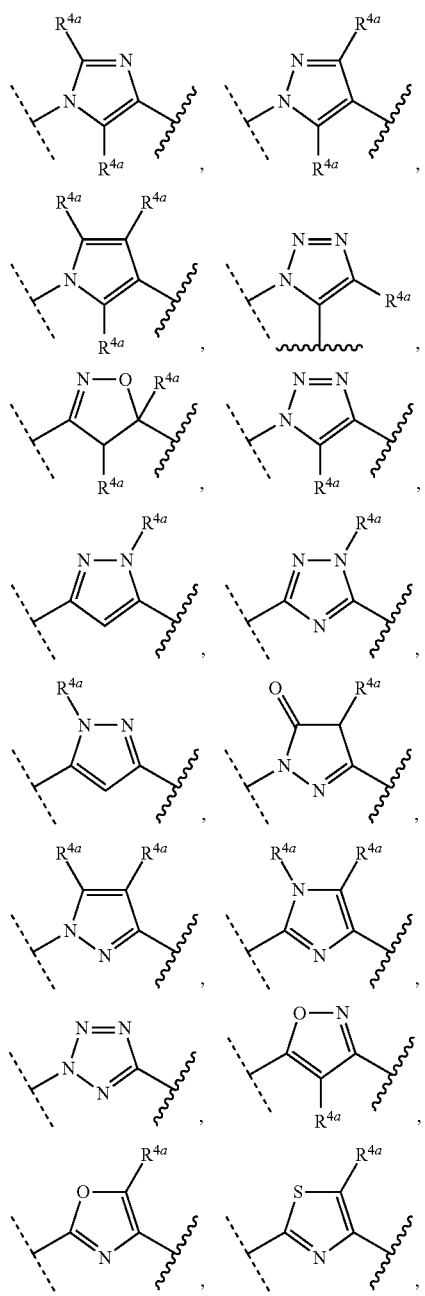

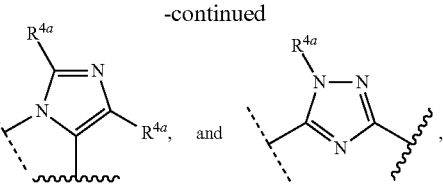

wherein $R^{4a}$ is hydrogen or $R^4$; $R^4$ is as defined in claim 1; and

"⁓⁓⁓" and "----" each represents the point of connection to the rest of the molecule.

In some embodiments, X is S. In some embodiments, $R^5$ is chloro or bromo.

In some embodiments, $R^5$ is chloro or bromo.

In some embodiments, X is S. In some embodiments, $R^5$ is —C≡CH.

In some embodiments, $R^{4a}$ is hydrogen. In some embodiments, $R^{4a}$ is $R^4$. In some embodiments, $R^4$ is independently selected from the group consisting of alkyl, halo, hydroxy, $C_{1-4}$ alkoxy, aryl, heteroaryl, and heterocycloalkyl, wherein the alkyl, aryl, heteroaryl, and heterocycloalkyl are optionally substituted with 1 to 3 $R^{11}$. In some embodiments, p is 1 and $R^4$ is $SOCH_3$ or $SO_2CH_3$.

In some embodiments, $R^2$ is selected from the group consisting of hydrogen, fluoro,

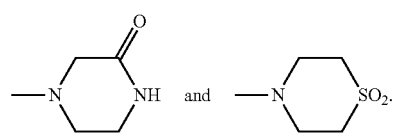

In some embodiments, the invention provides a method of preparing a compound of Formula III or a salt thereof or a hydrate of the compound or salt thereof

III

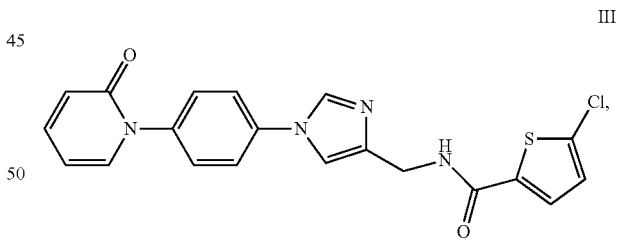

comprising contacting a compound of Formula III-A

III-A

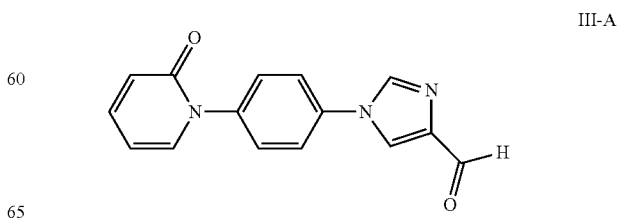

with a compound of Formula III-B

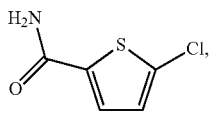
III-B under reaction conditions to form the compound of Formula III or the salt or the hydrate.

In some embodiments, the salt of the compound of Formula I, II, or III is a pharmaceutically acceptable salt.

In some embodiment, the process further comprising converting the salt of the compound of Formula I, II or III to a second salt of the compound of Formula I, II, or III, respectively, preferably the second salt is a pharmaceutically acceptable salt.

In some embodiments, the reaction conditions above comprise a solvent and a reducing agent. In some embodiments, the solvent is selected from the group consisting of toluene, NMP, DMF, xylene, hexane, cyclohexane, mesitylene and combinations thereof. In some embodiments, the reducing agent is selected from the group consisting of trialkylsilane, phenylsilane, trichlorosilane, polymethylhydrosiloxane, tris(trimethylsilyl)silane and combinations thereof. In some embodiments, the reducing agent is triethylsilane.

In some embodiments, the reaction conditions above further comprise an acid. In some embodiments, the acid is trifluoroacetic acid. In some embodiments, the acid is a Lewis acid, for example, BF$_3$, BF$_3$.Et$_2$O (boron trifluoride diethyl etherate), BF$_3$.Me$_2$O (boron trifluoride dimethyl etherate), FeCl$_3$, InCl$_3$, AlCl$_3$, or combinations thereof.

In some embodiments, the reaction conditions above further comprise an elevated temperature, such as about 80° C. to about 110° C. or about 90° C. to about 110° C.

In some embodiments, the compound of Formula III-A is prepared under reaction conditions comprising contacting a compound of Formula III-C

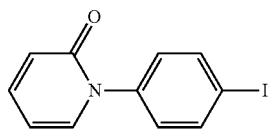
III-C with the compound of Formula III-D

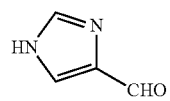
III-D to form the compound of Formula III-A.

In some embodiments, the reaction conditions of preparing the compound of Formula III-A further comprise a suitable solvent. In some embodiments, the reaction conditions of preparing the compound of Formula III-A further comprise copper (I) iodide (CuI). In some embodiments, the reaction conditions of preparing the compound of Formula III-A further comprise a ligand, for example proline or 8-hydroxy quinoline.

In some embodiments, the compound of Formula III-C is prepared under reaction conditions comprising contacting a compound of Formula III-E

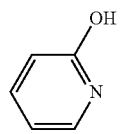
III-E with a compound of Formula III-F

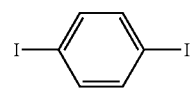
III-F to form the compound of Formula III-C.

In some embodiments, the reaction conditions of preparing the compound of Formula III-C comprise a suitable solvent. In some embodiments, the reaction conditions of preparing the compound of Formula III-C comprise a catalyst. In some embodiments, the catalyst is CuI. In some embodiments, the reaction conditions of preparing the compound of Formula III-C comprise a base. In some embodiments, the base is K$_2$CO$_3$ and Cs$_2$CO$_3$.

In some embodiments, the compound of Formula III-B is prepared under reaction conditions comprising converting the compound of Formula III-G

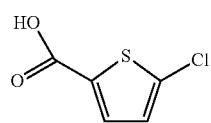
III-G to the compound of Formula III-B.

In some embodiments, the converting of the compound of Formula III-G to the compound of Formula III-B comprising a. converting the compound of Formula III-G to a compound of Formula III-H under reaction conditions to form the compound of Formula III-H:

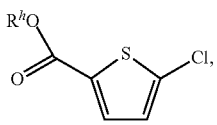
III-H wherein R$^h$ is methyl or ethyl; and b. converting the compound of Formula III-H to the compound of Formula III-B under reaction conditions to form the compound of Formula III-B.

In another aspect, this invention provides a method of preparing a salt of a compound of Formula III

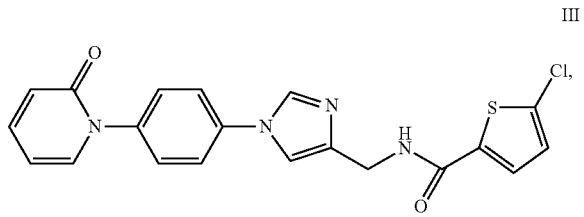 [SMILES: O=C(NCc1cn(-c2ccc(-n3ccccc3=O)cc2)cn1)c1ccc(Cl)s1]

comprising contacting a compound of formula III-A

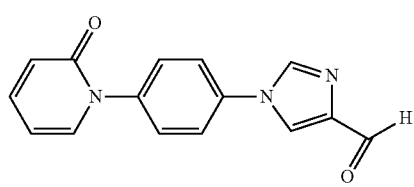

with a compound of formula III-B

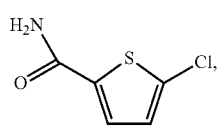

under reaction conditions to form the compound of formula III;

isolating the compound of Formula III under isolating conditions wherein the compound of Formula III is isolated as a free base; and forming the salt of the compound of Formula III under salt forming conditions comprising contacting the compound of Formula III with at least a molar equivalent of an acid in a solvent.

In some embodiments, the salt is a pharmaceutically acceptable salt. In some embodiments, the salt is in a crystalline form. U.S. Provisional Patent Application No. 61/287,683, filed on Dec. 17, 2009, and U.S. patent application Ser. No. 12/970,785, filed on Dec. 16, 2010, both of which are titled "Salts And Crystalline Forms of a Factor Xa Inhibitor," and U.S. Provisional Patent Application No. 61/287,681, filed on Dec. 17, 2009, and U.S. patent application Ser. No. 12/970,818, filed on Dec. 16, 2010, both of which are titled "Crystalline Forms of a Factor Xa Inhibitor," are incorporated by reference in their entirety.

In some embodiments, the acid is selected from the group consisting of hydrochloric, lactic, maleic, phenoxyacetic, propionic, succinic, adipic, ascorbic, camphoric, thiocyanic acid, 1-hydroxy-2-naphthoic acid, gluconic, phosphic, tartric, and citric acid.

In some embodiments, the acid is methanesulfonic acid.

In some embodiments, the solvent is a mixture of methylethylketone and tetrahydrofuran.

In some embodiments, the salt forming conditions further comprise a temperature of between about 40° C. and about 70° C.

The compound of Formula I, II or III can be converted to salts of various inorganic and organic acids. Examples of such salts include, but are not limited to, hydrochloride, lactate, maleate, phenoxyacetate, propionate, succinate, adipate, ascorbate, camphorate, gluconate, phosphate, tartrate, citrate, mesylate, fumarate, glycolate, naphthalene-1,5-disulphonate, 1-hydroxy-2-naphthoate, thiocynate, gentisate and benzene sulphonate. One of skill in the art will recognize that other acids can be used to make salts comprising the compound of Formula I that are useful in the present invention.

The compounds employed in the methods of this invention can be prepared from readily available starting materials. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts (1999) Protecting Groups in Organic Synthesis, 3rd Edition, Wiley, New York, and references cited therein.

Furthermore, the compounds of this invention may contain one or more chiral centers. Accordingly, if desired, such compounds can be prepared or isolated as pure stereoisomers, i.e., as individual enantiomers or diastereomers, or as stereoisomer-enriched mixtures. All such stereoisomers (and enriched mixtures) are included within the scope of this invention, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents, and the like.

The starting materials for the reactions are generally known compounds or can be prepared by known procedures or obvious modifications thereof. For example, many of the starting materials are available from commercial suppliers such as Aldrich Chemical Co. (Milwaukee, Wis., USA), Bachem (Torrance, Calif., USA), Emka-Chemce or Sigma (St. Louis, Mo., USA). Others may be prepared by procedures, or obvious modifications thereof, described in standard reference texts such as Fieser and Fieser's Reagents for Organic Synthesis, Volumes 1-15 (John Wiley, and Sons, 1991), Rodd's Chemistry of Carbon Compounds, Volumes 1-5, and Supplementals (Elsevier Science Publishers, 1989), Organic Reactions, Volumes 1-40 (John Wiley, and Sons, 1991), March's Advanced Organic Chemistry, (John Wiley, and Sons, 5th Edition, 2001), and Larock's Comprehensive Organic Transformations (VCH Publishers Inc., 1989).

The identity of the compounds or salts prepared by the present invention can be confirmed by nuclear magnetic resonance (NMR), Fourier transform infrared (FTIR) and mass spectrometry (MS). Purity and water content can be determined by reverse phase high-performance liquid chromatography (HPLC) and Karl Fischer titration method, respectively. Residue solvent content can be determined by gas chromatography (GC). The following are certain analytical methods that can be employed to determine the identity, purity and properties of compounds prepared by the methods of this invention.

Proton NMR,
FTIR,
Mass Spectroscopy,
HPLC for mesylate content,
Purity was determined based on related substances,
Karl Fischer for water content,
Trace metals and silicon analyses (inductively coupled plasma (ICP) Method),
Elemental analysis by combustion for carbon, hydrogen, nitrogen, by colorimetric titration for sulfur, and by ion chromatography for chlorine
GC for residual solvents.

These methods are generally known in the art. Exemplary procedures for these analytical methods are described in Example 5 below.

A number of methods are useful for the preparation of the salts described above and are known to those skilled in the art. For example, reaction of the compound of Formula I, II or III with one or more molar equivalents of the desired acid in a solvent or solvent mixture in which the salt is insoluble, or in a solvent like water after which the solvent is removed by evaporation, distillation or freeze drying. Alternatively, the compound of Formula I, Ia, II, or III may be passed over an ion exchange resin to form the desired salt or one salt form of the product may be converted to another using the same general process.

In addition, the method of the present invention for preparing the compound of Formula I, II or III on a gram-scale is substantially similar to the procedure used on the kilogram-scale.

III. Use of the Compounds

The compounds and/or salts prepared by the present invention can be used for preventing or treating a condition in a mammal characterized by undesired thrombosis by administering to the mammal a therapeutically effective amount of a compound or a pharmaceutically acceptable salt thereof prepared by this invention. The compounds and/or salts can be used either alone or in conjunction with pharmaceutically acceptable excipients to prevent the onset of a condition characterized by undesired thrombosis. The compounds and/or salts prepared by the present invention can also be used either alone or in conjunction with pharmaceutically acceptable excipients as prophylactic treatment for patients where the condition is not detected sufficiently early to prevent onset.

The compounds and/or salts prepared by this invention are characterized by their ability to inhibit thrombus formation with acceptable effects on classical measures of coagulation parameters, platelets and platelet function, and acceptable levels of bleeding complications associated with their use. Conditions characterized by undesired thrombosis would include those involving the arterial and venous vasculature.

The compounds and/or salts prepared by the present invention I are useful in treating thrombosis and conditions associated with thrombosis. The compounds and/or salts prepared by the present invention, selected and used as disclosed herein, are believed to be useful for preventing or treating a condition characterized by undesired thrombosis, such as (a) the treatment or prevention of any thrombotically mediated acute coronary syndrome including myocardial infarction, unstable angina, refractory angina, occlusive coronary thrombus occurring post-thrombolytic therapy or post-coronary angioplasty, (b) the treatment or prevention of any thrombotically mediated cerebrovascular syndrome including embolic stroke, thrombotic stroke or transient ischemic attacks, (c) the treatment or prevention of any thrombotic syndrome occurring in the venous system including deep venous thrombosis or pulmonary embolus occurring either spontaneously or in the setting of malignancy, surgery or trauma, (d) the treatment or prevention of any coagulopathy including disseminated intravascular coagulation (including the setting of septic shock or other infection, surgery, pregnancy, trauma or malignancy and whether associated with multi-organ failure or not), thrombotic thrombocytopenic purpura, thromboangiitis obliterans, or thrombotic disease associated with heparin induced thrombocytopenia, (e) the treatment or prevention of thrombotic complications associated with extracorporeal circulation (e.g. renal dialysis, cardiopulmonary bypass or other oxygenation procedure, plasmapheresis), (f) the treatment or prevention of thrombotic complications associated with instrumentation (e.g. cardiac or other intravascular catheterization, intra-aortic balloon pump, coronary stent or cardiac valve), and (g) those involved with the fitting of prosthetic devices.

In some embodiments, compounds and/or salts prepared by this invention are useful in: prevention of stroke in atrial fibrillation patients; prevention of thrombosis in medically ill patients; prevention and treatment of deep vein thrombosis; prevention of arterial thrombosis in acute coronary syndrome patients; and/or secondary prevention of myocardial infarction, stroke or other thrombotic events in patients who have had a prior event.

The compounds and/or salts prepared by this invention can also be used whenever inhibition of blood coagulation is required such as to prevent coagulation of stored whole blood and to prevent coagulation in other biological samples for testing or storage. Thus coagulation inhibitors prepared by this invention can be added to or contacted with stored whole blood and any medium containing or suspected of containing plasma coagulation factors and in which it is desired that blood coagulation be inhibited, e.g. when contacting the mammal's blood with material selected from the group consisting of vascular grafts, stents, orthopedic prosthesis, cardiac prosthesis, and extracorporeal circulation systems.

Besides being useful for human treatment, these compounds and/or salts are also useful for veterinary treatment of companion animals, exotic animals and farm animals, including mammals, rodents, and the like. More preferred animals include horses, dogs, and cats.

EXAMPLES

Unless stated otherwise, the abbreviations used throughout the specification have the following meanings:
A %=total percent area
aq.=aqueous
Ar=aryl or heteroaryl
AUC=area under curve
$CH_3SO_3H$=methanesulfonic acid
cm=centimeter
CuI=copper (I) iodide
d=doublet
deg=degree
DIPEA=diisopropylethylamine
DMSO=dimethyl sulfoxide
DSC=differential scanning calorimetry
EDTA=ethylenediaminetetraacetic acid
eq. or equiv=equivalent
$Et_3SiH$=triethyl silane
EtOAc=ethyl acetate EtOH=ethanol
g=gram
H$_2$SO$_4$=sulfuric acid
HPLC=high performance liquid chromatography
hr=hour
Hz=hertz
FTIR=Fourier transform infrared
IC=ion chromatography
ICP=inductively coupled plasma
IPA=Isopropanol
IR=infrared
J=coupling constant
K$_2$CO$_3$=potassium carbonate
kg=kilogram
L=liter
LOD=limit of detection
M=molar
m=multiplet
mA=milliampere
Me=methyl
MeCN=acetonitrile
MEK=methyl ethyl ketone
MeO=methoxy
MeOH=methanol
MeTHF=methyltetrahydrofuran
mg=milligram
min.=minute
mL=milliliter
mm=millimeter
mmHg=millimeters of mercury
MTBE=methyl tert butyl ether
N=normal
Na$_2$SO$_4$=sodium sulfate
NH$_3$=ammonia
nM=nanomolar
NMR=nuclear magnetic resonance
oop=out-of-plane vibration
PhMe=toluene
ppm=parts per million
RH=relative humidity
rpm=revolutions per minute
r.t.=room temperature
s=singlet
TGA=thermal gravimetric analysis
TDS=total dissolved solids
TFA=trifluoroacetic acid
THF=tetrahydrofuran
Wt=weight
μM=micromolar Example 1

Preparation of Compound III-C

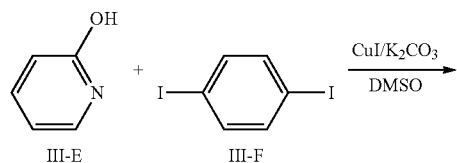

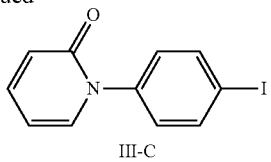

III-C 121.1 kg of 1,4-diiodobenzene III-F (367 mol) was charged as a solid to a 200-gallon reactor containing DMSO followed by 35 kg of 2-hydroxypyridine III-E (368 mol), 123 kg of K$_2$CO$_3$ (4.8 equiv), and 7.3 kg CuI (0.1 equiv). The mixture was heated to 120±5° C. for 3 hours. The reaction monitored by HPLC for completion. The reaction after cooling was quenched with water and EtOAc. The organic layer was washed with brine followed by Na$_2$SO$_4$ drying. After filtration, the EtOAc layer was concentrated at 85° C. followed by addition of heptanes. The slurry was then cooled to 20° C. for 1 hour and isolated via a cleaned and dried centrifuge. The product was collected and dried for 16 hours at 35° C. under about 28 mmHg. Recovery was 55.1 kg (50% yield) of Compound III-C, with 85.9% AUC purity.

Example 2

Preparation of Compound III-A

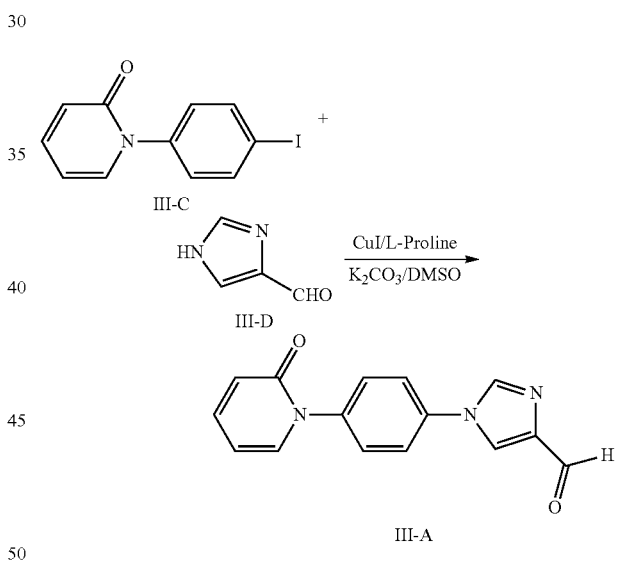

CuI (2.95 kg, 0.20 equiv) and L-proline (1.88 kg, 0.20 equiv) were mixed for 15 minutes in DMSO (253 kg). To this was added Compound III-C (24 kg, 1.0 equiv), K$_2$CO$_3$ (22.8 kg, 4.1 equiv), and 4-formylimidazole III-D (8.30 kg, 1.07 equiv). The reaction mixture was then heated to 120±5° C. for 3.5 hours. HPLC analysis concluded the reaction was complete and the mixture was cooled to 20±5° C. The reaction was diluted with water (40 volumes) and dichloromethane (DCM) (20 volumes), stirred for 1 hour, and centrifuged. In order to remove the insoluble impurities, the centrifuge filtrates were then polished filtered across a press fitted with 1-micron paper. The layers were separated, organic layer dried with Na$_2$SO$_4$, and filtered. The organic filtrates were atmospherically distilled to reduce the volume, charged with EtOAc, and continued to distill to an internal temperature of about 72° C. The product slurry was cooled to about 20° C. for 2 hours and isolated 6.5 kg of the aldehyde intermediate Compound III-A (30.4% yield).

Example 3

Preparation of Compound III-B

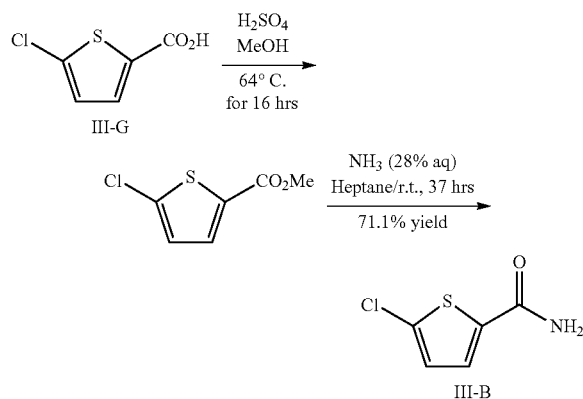

The 200-gallon reactor was charged with methanol (135 kg, 14.3 volumes), 5-chlorothiophene-2-carboxylic acid III-G (12 kg, 73.81 mol, 1.0 equiv), and sulfuric acid (6.7 kg, 68.31 mol) under nitrogen. The contents were warmed to reflux (64° C.) for 16 hours and reaction completion monitored by HPLC. The reactor was cooled to 40° C. and the mixture was vacuum distilled to an oil at <50° C. The methyl ester obtained was cooled to 20° C. and ammonium hydroxide (157 kg, 2586 mol, 35.2 equiv) was charged along with heptane (10 kg) to the reactor. The reactor contents were mixed for 36 hours at ambient temperature. The completion of the reaction was monitored by HPLC for the disappearance of methyl ester intermediate. The precipitated solids were centrifuged and washed with water followed by heptane. The isolated solids were dried at 45° C. for 14 hours to afford Compound III-B (8.42 kg, 77.1% yield).

Example 4

Preparation of Compound III

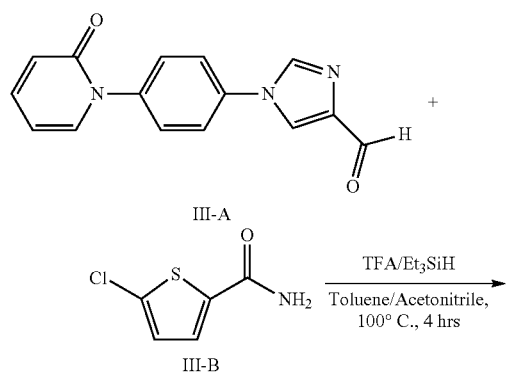

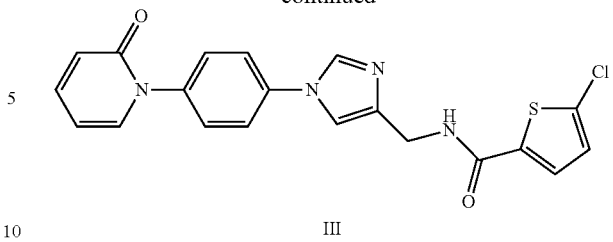

A nitrogen-inerted 200-gallon reactor was charged with toluene (202.4 kg, 20 volumes), 1-(4-(2-oxopyridin-1(2H)-yl)phenyl)-1H-imidazole-4-carbaldehyde (Compound III-A, 11.7 kg, 1.0 equiv) and 2-amido-5-chlorothiophene (Compound III-B, 7.8 kg, 1.09 equiv). The contents were mixed together for 15 minutes followed by the addition of triethylsilane (Et$_3$SiH) (15.3 kg, 3.0 equiv) and trifluoroacetic acid (15.3 kg, 3.0 equiv). The reaction mixture was heated at 100±5° C. for 4 hours and the reaction monitored by HPLC analysis. The reaction was complete when Compound III-A was less than 1%. The reaction mixture was cooled to 40±5° C. and acetonitrile (139.2 kg) was added and reaction further cooled to 15±5° C. While maintaining the temperature at or below about 35° C., diisopropylethylamine (DIPEA) (18.7 kg, 3.3 equiv) was added over 15 minutes. The reaction contents were stirred for 1 hour at 20° C. and the solid Compound III isolated on a centrifuge. The collected free base of Compound III was vacuum dried at 45° C. and 28 mmHg for 32 hours. Compound III (10.89 kg, 60.2% yield) was collected as tan solid. HPLC record purity as area %: 93.5%. Structure was confirmed by Infrared (IR) spectrum using the procedure as described below.

Example 5

Preparation of Methanesulfonate (Mesylate) Salt of Compound III

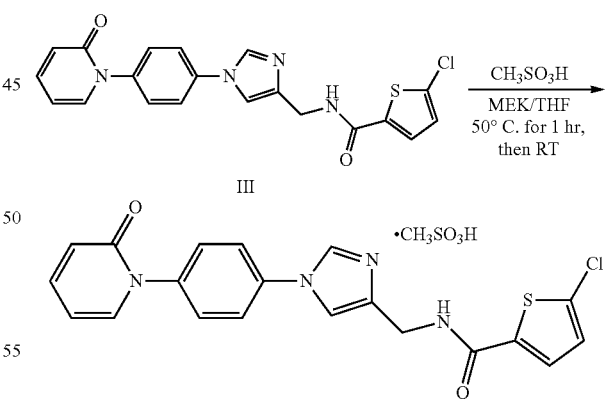

A slurry of free base of Compound III (10.89 kg, 1.0 equiv) in methylethyl ketone (MEK, 217 kg) was mixed for 30 minutes. To this slurry a THF solution (27.2 kg, 2.8 volumes) of methanesulfonic acid (MeSO$_3$H) (2.72 kg, 1.07 equiv) was added and the mixture heated at 50° C. for 1 hour. The mixture was cooled to 20° C. and stirred for 30 minutes. The mesylate salt was centrifuged and washed with MEK (32.7 kg). The product was dried at 45° C. under 28 mmHg vacuum for 116 hours and further dried at 61° C. for 60 hours. After drying, 12.5 kg the mesylate salt of Compound III (95% yield) was isolated in crystalline Form A. The structure of the compound obtained was analyzed by mass spectrometry, NMR and IR.

Mass Spectrometry

Mass spectrometry in negative ion mode gave a 505.0 ion which corresponds to M-1 for the exact mass of mesylate of Compound III (506.1). In positive ion mode a 411.1 ion was found which corresponds to the exact mass of 410.06 for the free base of Compound III.

Nuclear Magnetic Resonance Spectrum (NMR)

The proton NMR spectrum of the mesylate salt of Compound III was obtained after dissolving a sample in deuterated dimethyl sulfoxide (DMSO-$d_6$). All observed chemical shifts were consistent with the structure of mesylate salt of Compound III. The assignments of protons and the multiplicity pattern are provided below in Table 1. The $^1$H NMR spectrum was done on Bruker 400 MHz instrument in DMSO-$d_6$ by Bruker AXS Inc., Madison, Wis., USA.

TABLE 1

Proton Assignment and Multiplicity Pattern of the Mesylate Salt of Compound III

| Chemical Shift (ppm) | Proton Assignment |
|---|---|
| 2.21 (s, 3H) | CH$_3$ of Mesylate |
| 4.55 (s, 2H) | H9 |
| 6.36 (dd, 1H) | H3 |
| 6.50 (d, 1H) | H1 |
| 7.22 (d, 1H) | H10 |
| 7.54 (m, 1H) | H2 |
| 7.67 (d, 1H) | H4 |
| 7.69 (d, 1H) | H6 |
| 7.70 (d, 1H) | H11 |
| 7.92 (d, 2H) | H5 |
| 8.22 (s, 1H) | H7 |
| 9.25 (s, 1H) | NH of the amide |
| 9.54 (s, 1H) | H8 |

Infrared Spectrum

Infra-red (IR) absorption spectrum of the mesylate of Compound III was determined as KBr pellet. The assignment of characteristic absorption bands are tabulated in Table 2.

TABLE 2

IR Absorption Bands for the Mesylate Salt of Compound III

| Frequency (cm$^{-1}$) | Intensity | Sub-Structure |
|---|---|---|
| 3277 & 3133 | weak | N—H bond |
| 1660 & 1648 | Medium | C=O stretch in secondary amides, generally strong, ~1650-1685 cm$^{-1}$ in NHC=O; |
| 1535 | Medium | N—C=O stretch in secondary amide |
| 1428 | Medium | CH$_2$ bend in NCH$_2$ |
| 1311 | Medium | S(=O) stretch generally absorption near 1300 and 1125 cm$^{-1}$ |
| 1212 | Strong | C—N stretch in secondary amides, generally strong, ~1250 cm$^{-1}$ in NHC=O |
| 1164 | Strong | C—Cl stretch |
| 1038 | Strong | C—Cl stretch |
| 944 | weak | CH bend |

TABLE 2-continued

IR Absorption Bands for the Mesylate Salt of Compound III

| Frequency (cm$^{-1}$) | Intensity | Sub-Structure |
|---|---|---|
| 843 & 775 | Medium | =CH bend (oop), many bands, ~1005-675 cm$^{-1}$ ArC—H bend (oop), |
| 758 | Medium | NH bend (oop), ~700 cm$^{-1}$ in NHC=O |

X-Ray Powder Diffraction patterns were collected on a Bruker AXS C2 GADDS diffractometer by Bruker AXS Inc., Madison, Wis., USA using Cu Kα radiation (40 kV, 40 mA), automated XYZ stage, laser video microscope for auto-sample positioning and a HiStar 2-dimensional area detector. X-ray optics consists of a single Gael multilayer mirror coupled with a pinhole collimator of 0.3 mm.

The beam divergence, i.e. the effective size of the X-ray beam on the sample, was approximately 4 mm. A θ-θ continuous scan mode was employed with a sample-detector distance of 20 cm which gives an effective 2θ range of 3.2°-29.7°. Typically the sample would be exposed to the X-ray beam for 120 seconds. XRPD pattern of Form A is shown in FIG. 1.

Example 6

Recrystallization of Methanesulfonate (Mesylate) Salt of Compound III

Figure 2:
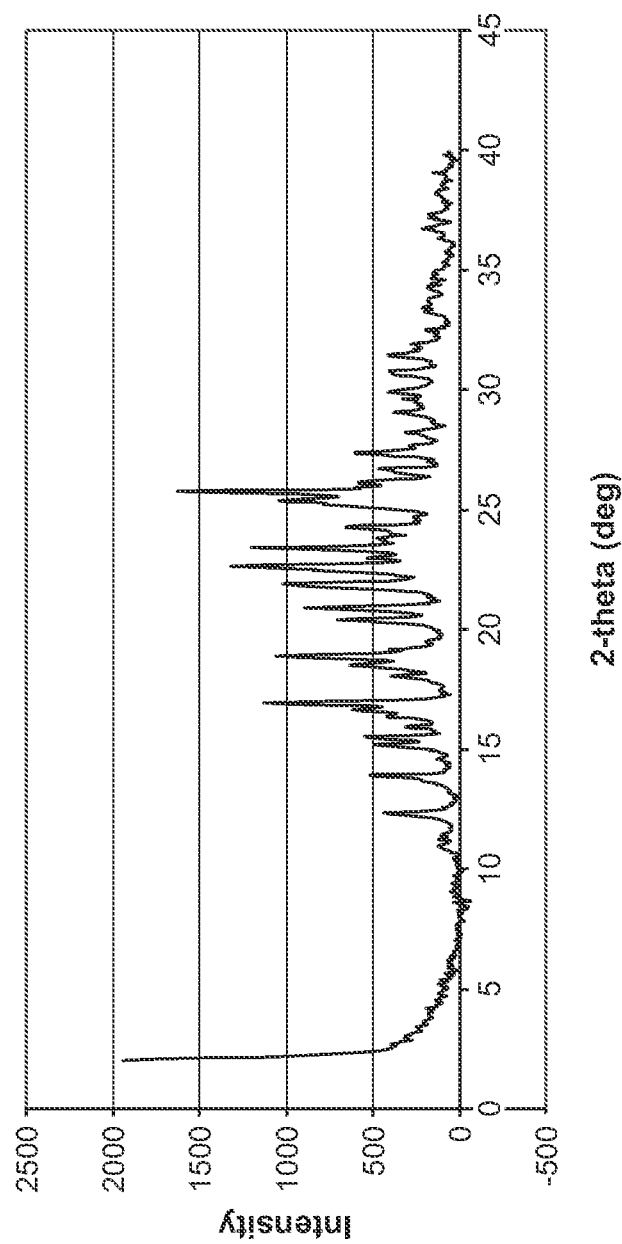
FIG. 2 provides an XRPD pattern of crystalline Form B of the mesylate salt of the compound of Formula III.

The mesylate salt of Compound III 2.70 kg was charged to a glass-lined reactor, followed by acetone (39.70 kg), and USP water (4.35 kg). The solution was refluxed at 58° C. for approximately 1 hour followed by hot polish filtration through 0.2-micron cartridge filter. The polished filtrate was cooled to 20±5° C. followed by addition of methylethylketone (MEK) (32.80 kg) and stirred for 12 hours at ambient temperature. The slurry was cooled to 0-5° C. for more than 2 hours and then filtered through a filtration funnel. The solid isolated was dried at 50±5° C. under vacuum for at least 16 hours to afford the mesylate salt of Compound III (1.7 kg) as a tan crystalline Form B. XRPD pattern of Form B is shown in FIG. 2.

Example 7

Preparation of Form C of Compound III Mesylate Salt

Figure 3:
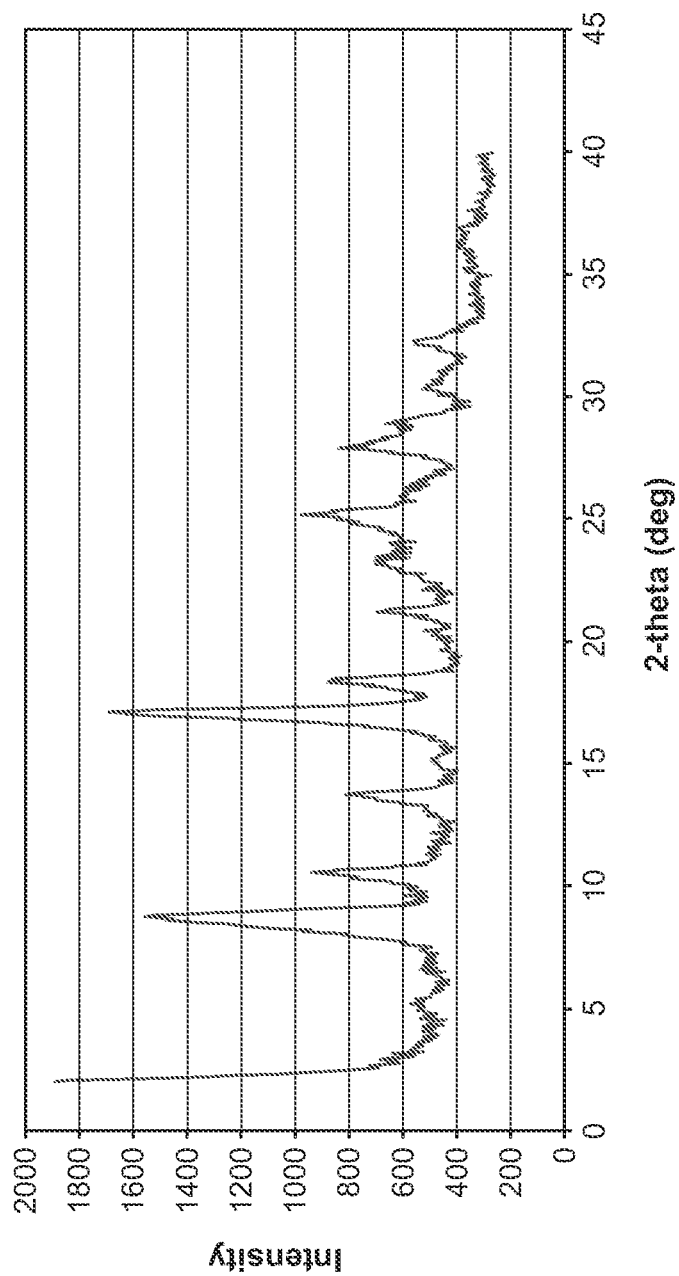
FIG. 3 provides an XRPD pattern of crystalline Form C particles of the mesylate salt of the compound of Formula III isolated from aqueous slurries of Form A after refrigerated storage overnight.

A formulation comprises of crystalline Form A of Compound III mesylate salt up to 100 mg/mL suspended in an aqueous vehicle of 0.3% methylcellulose, 0.5% polysorbate 80, and 0.25% simethicone. Since Compound III is difficult to wet and disperse, especially at high doses, a planetary mixer (e.g., "THINKY" a mixer by THINKY Corp.) was used. At 100 mg/mL Compound III, the suspension was off white in color, very thick and flow poorly immediately after mixing. However, after brief storage (<1 hour) at refrigerated condition, the suspension became free-flowing. It was found that the Form A of Compound III changed to a different white crystalline Form C (XRPD shown in FIG. 3). It has been found that effective mixing of Form A of Compound I under high shear, such as by a THINKY mixer or using a homogenizer or ball milling facilitates fast and complete conversion of Form A to Form C. Crystalline Form C is both physically and chemically stable at refrigerated condition for at least one week.

Example 8

Preparation of Form D of Compound III Mesylate Salt

Figure 4:
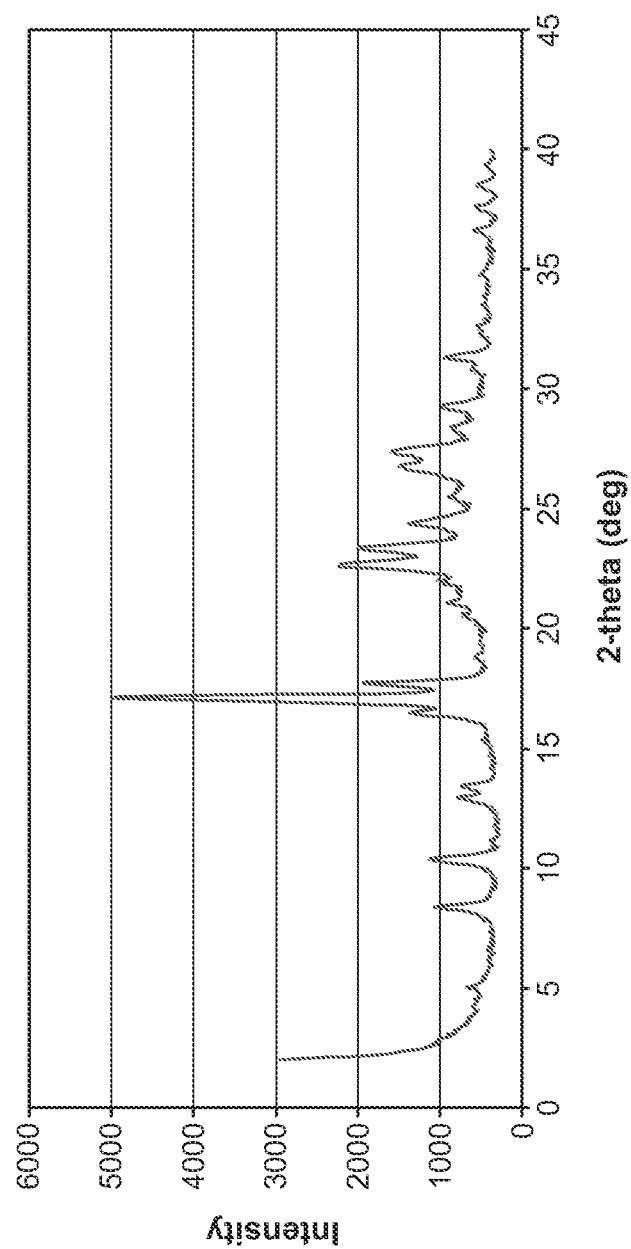
FIG. 4 provides an XRPD pattern of crystalline Form D particles of the mesylate salt of the compound of Formula III isolated from aqueous slurries of Form A after multiple cycles of −20° C. freezing and thawing during dosing formulation for toxicity studies.

In another experiment, a formulation of 100 mg/mL Form A of Compound III mesylate salt did not become free-flowing, i.e., did not convert to Form C after storage at refrigerated condition. In order to obtain a dosable formulation, the procedure was revised to include free-flowing crystalline form and multiple freezing (at −20° C.)-thawing-mixing cycles to speed up the conversion. After this process, a free-flowing crystalline form was obtained having a unique XRPD pattern and was named Form D (XRPD shown in FIG. 4).

Example 9

Preparation of Form E of Compound III Mesylate Salt

Figure 5:
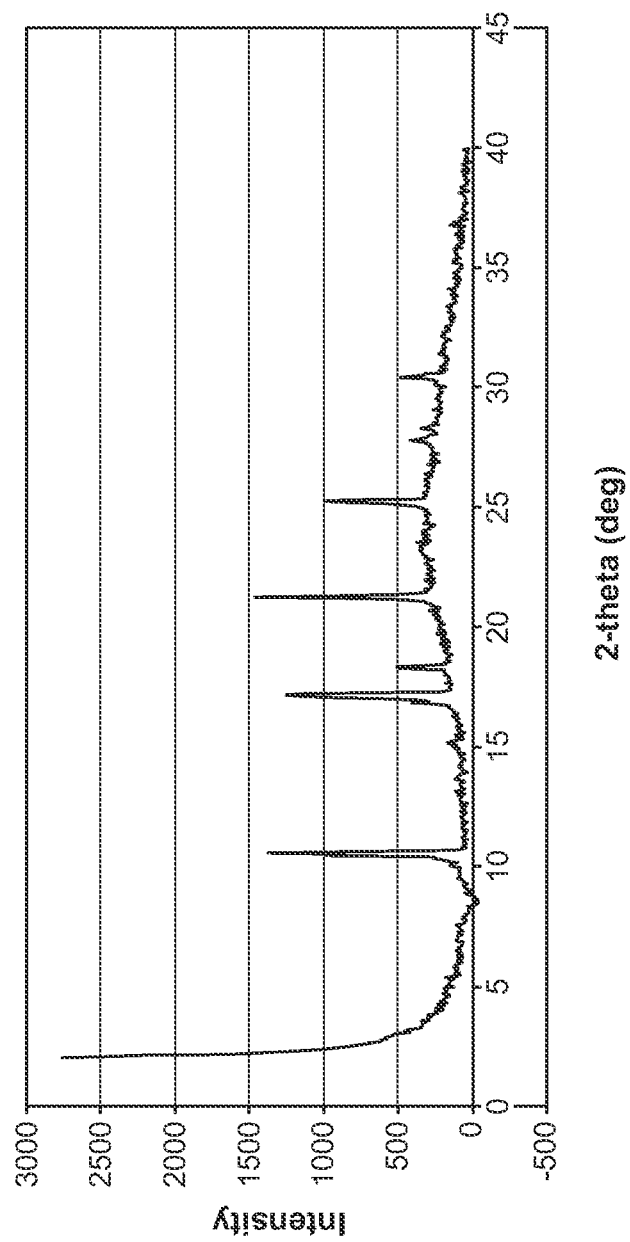
FIG. 5 provides an XRPD pattern of crystalline Form E particles (needle shaped) of the mesylate salt of the compound of Formula III isolated from aqueous slurries of Form B after overnight storage at room temperature.

The crystalline Form B of the mesylate salt of Compound III after dispersing in water, overnight at room temperature, converted partially to a needle shaped crystalline Form E with a distinctive XRPD pattern (FIG. 5).

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference.

What is claimed is:

1. A method of preparing a compound of Formula III or a salt of the compound

III

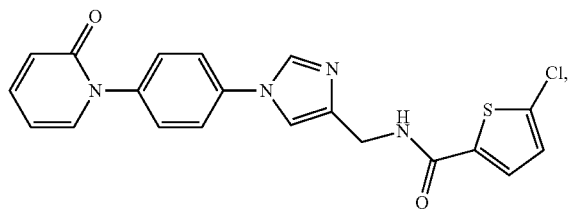

comprising contacting a compound of Formula III-A

III-A

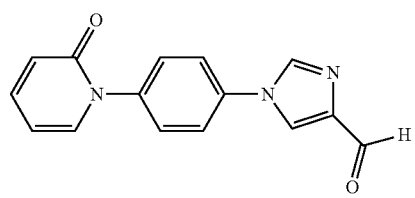

with a compound of Formula III-B

III-B

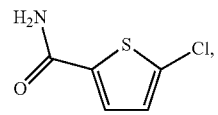

in presence of a solvent and a reducing agent to form the compound of Formula III or the salt thereof.

2. The method of claim 1, wherein the solvent is selected from the group consisting of toluene, N-methyl-2-pyrrolidone, dimethyl formamide, xylene, hexane, cyclohexane, mesitylene and combinations thereof.

3. The method of claim 2, wherein the reducing agent is selected from the group consisting of trialkylsilane, phenylsilane, trichlorosilane, polymethylhydrosiloxane, tris(trimethylsilyl)silane and combinations thereof.

4. The method of claim 3, wherein the reducing agent is triethylsilane.

5. The method of claim 3, wherein the method further comprises an acid.

6. The method of claim 5, wherein the acid is trifluoroacetic acid.

7. The method of claim 5, wherein the acid is a Lewis acid.

8. The method of claim 7, wherein the acid is selected from the group consisting of $BF_3.Et_2O$, $FeCl_3$, $InCl_3$, $AlCl_3$, and combinations thereof.

9. The method of claim 5, wherein the method further comprises an elevated temperature.

10. The method of claim 9, wherein the elevated temperature is 80° C. to 110° C.

11. The method of claim 9, wherein the elevated temperature is 90° C. to 110° C.

12. The method of claim 1, wherein the compound of Formula III-A is prepared by contacting a compound of Formula III-C

III-C

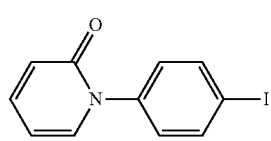

with the compound of Formula III-D

III-D

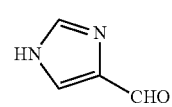

in presence of copper (I) iodide to form the compound of Formula III-A.

13. The method of claim 12, wherein the compound of Formula III-C is prepared by contacting a compound of Formula III-E

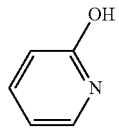
III-E with a compound of Formula III-F

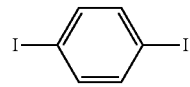
III-F in presence of copper (I) iodide to form the compound of Formula III-C.

14. The method of claim 1, wherein the compound of Formula III-B is prepared from the compound of Formula III-G

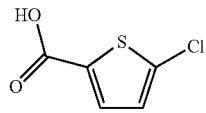
III-G by a method comprising a. preparing a compound of Formula III-H:

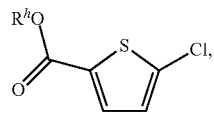
III-H from the compound of Formula III-G via esterification, wherein $R^h$ is methyl or ethyl; and b. preparing the compound of Formula III-B from the compound of Formula III-H by reacting with $NH_3$.

15. The method of claim 1, further comprising contacting the compound of Formula III with an acid to give a salt of the compound of Formula III.

16. A method of preparing a pharmaceutically acceptable salt of a compound of Formula III

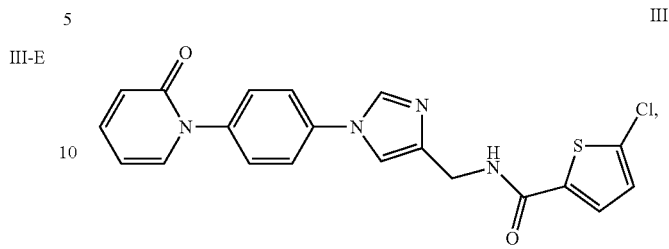
III comprising contacting a compound of formula III-A

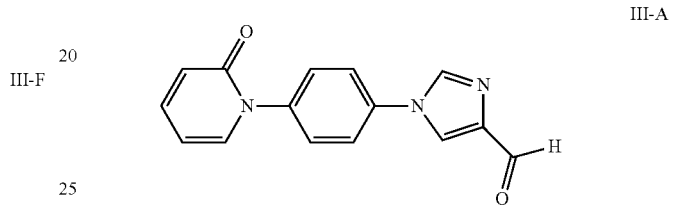
III-A with a compound of formula III-B

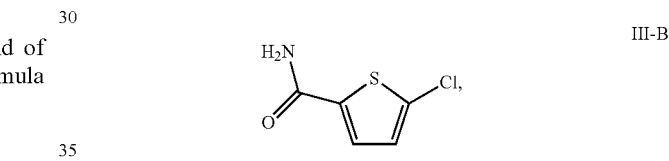
III-B in presence of a solvent and a reducing agent to form the compound of Formula III;

isolating the compound of Formula III as a free base; and forming the pharmaceutically acceptable salt of the compound of Formula III by contacting the compound of Formula III with at least a molar equivalent of an acid in a solvent.

17. The method of claim 16, further comprising recovering the pharmaceutically acceptable salt.

18. The method of claim 16, wherein the acid is selected from the group consisting of hydrochloric, lactic, maleic, phenoxyacetic, propionic, succinic, adipic, ascorbic, camphoric, gluconic, phosphic, tartric, and citric acid.

19. The method of claim 16, wherein the acid is methanesulfonic acid.

20. The method of claim 19, wherein the solvent for contacting the compound of Formula III with at least a molar equivalent of an acid comprises methylethylketone and tetrahydrofuran.

21. The method of claim 19, wherein the solvent for contacting the compound of Formula III with at least a molar equivalent of an acid comprises acetone and water.

22. The method of claim 20, wherein the method further comprises a temperature of between 40° C. and 70° C.

23. The method of claim 19, wherein the salt of the compound of Formula III is recovered in a crystalline form.

* * * * *